(12) United States Patent
Bulla

(10) Patent No.: US 6,423,502 B2
(45) Date of Patent: *Jul. 23, 2002

(54) METHOD FOR SCREENING CANDIDATE PESTICIDES USING A RECEPTOR THAT BINDS *BACILLUS THURINGIENSIS* TOXIN

(75) Inventor: Lee A. Bulla, Richardson, TX (US)

(73) Assignee: University of Wyoming, Laramie, WY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/178,176

(22) Filed: Oct. 23, 1998

Related U.S. Application Data

(62) Division of application No. 08/982,129, filed on Dec. 1, 1997, now Pat. No. 6,007,981, which is a division of application No. 08/326,117, filed on Oct. 19, 1994, now Pat. No. 5,693,491.

(51) Int. Cl.$^7$ .................. G01N 33/566; C12N 15/12; C12N 5/10; C07K 14/705; C07K 14/325
(52) U.S. Cl. .................. 435/7.21; 435/7.2; 435/325; 435/320.1; 435/69.1; 435/252.3; 435/254.11; 530/300; 530/350; 536/23.1; 536/23.5; 536/23.71
(58) Field of Search .................. 435/69.1, 320.1, 435/325, 348, 252.3, 254.11, 7.2, 7.21; 536/23.1, 23.5, 23.71; 530/300, 350

(56) References Cited

U.S. PATENT DOCUMENTS

| | | | |
|---|---|---|---|
| 4,675,285 A | 6/1987 | Clark et al. | 435/6 |
| 5,071,654 A | 12/1991 | English | 424/405 |

FOREIGN PATENT DOCUMENTS

| | | |
|---|---|---|
| WO | WO 96 12964 | 5/1996 |

OTHER PUBLICATIONS

Oddou et al., Immunologically unrelated Heliothis sp. and Spodoptera sp. midgut membrane–proteins bind *Bacillus thuringiensis* CryIA(b) delta–endotoxin, Eur. J. Biochem., 212: 145–150, 1993.*
Almond et al., Suppression of Protein Structure Destabilizing Mutations in *Bacillus thuringiensis* δ–endotoxin by Second Site Mutations; Biochemistry 32:1040–1046 (1993).
Chen et al., Site–directed mutations in a highly conserved region of *Bacillus thuringiensis* δ–endotoxin affect inhibition of short circuit current across Bombyx mori midguts, Proc. Natl. Acad. Sci. USA 90:9041–9045 (1993).
Sorsch, J. A. et al., "Determination of the specific region of BT–R1 to which the CryaAb toxin of *Bacillus thuringiensis* susp. Berliner binds", *FASEB Journal (Abstracts)*, vol. 11, No. 9, Jul. 31, 1997, p. A1050.

English, L., Mode of action of delta–endotoxins from *Bacillus Thuringiensis*: A comparison with other bacterial toxins, Insect Biochem. Molec. Biol. 22(1):1–7.
Gill et al., The Mode of Action of *BacillusThuringiensis* Endotoxins; Ammun. Rev. Entomol. (1992) 37:615–36.
Hoffman et al., Specificity of *Bacillus Thuringiensis* δ–endotoxins is Correlated with the Presence of High–affinity Binding Sites in the Brush Border Membrane of Target Insect Midguts; Proc. Natl. Acad. Sci., USA (1988) 85:7844–7848.
Hofte et al., Insecticidal Crystal Proteins of *Bacillus Thuringiensis*; Microbiological Reviews (1989) 53(2):242–255.
Ishihara et al., Molecular cloning and expression of a cDNA encoding the secretin receptor, EMOB J., vol. 10, No. 7, 1635–1641.
Knight et al., The eceptor for *Bacillus thuringiensis* CrylA(c) delta–endotoxin in the brush border membrane of the lepidopteran *Manduca sexta* is aminopeptidase N, Molecular Microbiology (1994) 11(3):429–436 (1994).
Knowles et al., The crystal δ–endotoxins of *Bacillus thuringiensis*: Models for their mechanism of action on the insect gut, BioEssays 15(7): 469–476 (1993).
Lee et al., Location of a *Bombyx mori* Receptor Binding Region on a *Bacillus thuringiensis* δ–Endotoxin, J. Biol. Chem., vol. 167, No. 5, pp. 3115–3121 (1992).
Sanchis et al., Identification and partial purification of a *Bacillus thuringiensis* CryIC δ–endotoxin binding protein from *Spodoptera littoralis* gut membranes, FEBS 316(3):264–268 (1993).
Sangadala et al., A Mixture of *Manduca Sectra* Aminopeptidase and Phosphatase Enhances *Bacillus Thuringiensis* Insecticidal CrylA(c) Toxin Biding and Rb$^+$–K$^+$ Efflux in vitro, vol. 269, No. 13, pp. 10088–10092 (1994).
Vadlamudi et al., Cloning and Expression of a Receptor for an insecticidal Toxin of *Bacillus thuringiensis*, J. Biol. Chem. 270(10):5490–5494 (1995).
Vadlamudi et al., A Specific Binding Protein from *Manduca Sexta* for the Insecticidal Toxin of *Bacillus Thuringiensis* Subsp., Berliner, J. Biol. Chem. 268(17):12334–12340 (1993).
Van Rie et al., Specificity of *Bacillus Thuringiensis* δ–endotoxins; Eur. J. Biochem. (1989) 186:239–247.
Van Rie et al., Receptors on the Brush Border Membrane of the Insect Midgut as Determinants of the Specificity of *Bacillus Thuringiensis* Belta–Endotoxins (1990) 56(5):1378–1385.

* cited by examiner

Primary Examiner—Lorraine Spector
Assistant Examiner—Claire M. Kaufman
(74) Attorney, Agent, or Firm—Morrison & Foerster LLP

(57) ABSTRACT

The cDNA that encodes a glycoprotein receptor from the tobacco hornworm which binds a *Bacillus thuringiensis* toxin has been obtained and sequenced. The availability of this cDNA permits the retrieval of DNAs encoding homologous receptors in other insects and organisms as well as the design of assays for the cytotoxicity and binding affinity of potential pesticides and the development of methods to manipulate natural and/or introduced homologous receptors and, thus, to destroy target cells, tissues and/or organisms.

2 Claims, 22 Drawing Sheets

SEQ ID NO. 1

```
         10         20         30         40
GACCAATCGGAGTGTGGTGAATTTTTGGAAAATATTTTGTGCGGTTCC
     50         60         70         80         90
TTTAGTTGTGTAATATAGTACTTTAGTTACAAATTTGGAATAATTTGG
    100        110        120        130        140
CAGCAAAACCATCTGCAGCAACAAAATCATCTGCAGCTGCGAAATCAT
    150        160        170        180        190
CTGCAGCAGCAAAAGCATCTTCAGGAGCGAGAAAAGCCCCAAATAATG
              200        210        220
TGAG   ATG GCA GTT GAC GTC CGA ATC GCT GCC TTC
       Met Ala Val Asp Val Arg Ile Ala Ala Phe
     230        240        250        260
CTG CTG GTG TTT ATA GCG CCT GCA GTT TTA GCT CAA
Leu Leu Val Phe Ile Ala Pro Ala Val Leu Ala Gln
        270        280        290
GAG AGA TGT GGG TAT ATG ACC GCC ATC CCA AGG CTA
Glu Arg Cys Gly Tyr Met Thr Ala Ile Pro Arg Leu
 300        310        320        330
 CCA CGA CCG GAT AAT TTG CCA GTA CTA AAT TTT GAA
 Pro Arg Pro Asp Asn Leu Pro Val Leu Asn Phe Glu
      340        350        360        370
GGC CAG ACA TGG AGT CAG AGG CCC CTG CTC CCC GCC
Gly Gln Thr Trp Ser Gln Arg Pro Leu Leu Pro Ala
         380        390        400
CCG GAG CGG GAT GAC CTG TGC ATG GAC GCC TAC CAC
Pro Glu Arg Asp Asp Leu Cys Met Asp Ala Tyr His
  410        420        430        440
GTG ATA ACA GCC AAC CTC GGC ACG CAG GTC ATC TAC
Val Ile Thr Ala Asn Leu Gly Thr Gln Val Ile Tyr
        450        460        470
ATG GAT GAA GAG ATA GAA GAC GAA ATC ACC ATC GCC
Met Asp Glu Glu Ile Glu Asp Glu Ile Thr Ile Ala
 480        490        500        510
 ATA CTT AAT TAT AAC GGA CCA TCA ACT CCG TTC ATT
 Ile Leu Asn Tyr Asn Gly Pro Ser Thr Pro Phe Ile
```

FIG. 1A

```
        520              530              540              550
GAA CTG CCA TTT TTA TCC GGT TCG TAC AAT CTG CTG
Glu Leu Pro Phe Leu Ser Gly Ser Tyr Asn Leu Leu
           560              570              580
ATG CCG GTC ATC AGG AGA GTT GAC AAC GGG GAG TGG
Met Pro Val Ile Arg Arg Val Asp Asn Gly Glu Trp
     590              600              610              620
CAT CTC ATC ATC ACG CAA AGA CAG CAT TAC GAG TTG
His Leu Ile Ile Thr Gln Arg Gln His Tyr Glu Leu
           630              640              650
CCC GGC ATG CAG CAG TAC ATG TTC AAT GTG CGC GTG
Pro Gly Met Gln Gln Tyr Met Phe Asn Val Arg Val
 660              670              680              690
 GAC GGC CAG TCG CTG GTG GCA GGC GTG TCT CTC GCT
 Asp Gly Gln Ser Leu Val Ala Gly Val Ser Leu Ala
     700              710              720              730
ATC GTC AAC ATA GAT GAC AAC GCG CCC ATC ATA CAA
Ile Val Asn Ile Asp Asp Asn Ala Pro Ile Ile Gln
           740              750              760
AAC TTC GAG CCT TGC CGG GTT CCT GAA CTG GGC GAG
Asn Phe Glu Pro Cys Arg Val Pro Glu Leu Gly Glu
   770              780              790              800
CCA GGG TTG ACA GAA TGC ACA TAC CAA GTA TCG GAC
Pro Gly Leu Thr Glu Cys Thr Tyr Gln Val Ser Asp
           810              820              830
GCG GAC GGA CGG ATC AGC ACA GAG TTC ATG ACG TTC
Ala Asp Gly Arg Ile Ser Thr Glu Phe Met Thr Phe
840              850              860              870
 AGG ATC GAC AGC GTT CGT GGC GAC GAG GAG ACC TTC
 Arg Ile Asp Ser Val Arg Gly Asp Glu Glu Thr Phe
     880              890              900              910
TAC ATC GAA CGG ACG AAT ATC CCC AAC CAA TGG ATG
Tyr Ile Glu Arg Thr Asn Ile Pro Asn Gln Trp Met
           920              930              940
TGG CTA AAT ATG ACC ATA GGC GTT AAT ACC TCG CTC
Trp Leu Asn Met Thr Ile Gly Val Asn Thr Ser Leu
```

FIG. 1B

```
      950              960           970            980
AAC TTC GTC ACC AGT CCG CTG CAT ATA TTC AGC GTG
Asn Phe Val Thr Ser Pro Leu His Ile Phe Ser Val
         990           1000            1010
ACA GCC CTG GAC TCG CTC CCG AAC ACC CAC ACG GTG
Thr Ala Leu Asp Ser Leu Pro Asn Thr His Thr Val
1020             1030           1040            1050
   ACT ATG ATG GTG CAA GTG GCG AAT GTG AAC AGC
   Thr Met Met Val Gln Val Ala Asn Val Asn Ser
             1060            1070           1080
CGT CCG CCG CGC TGG CTG GAG ATC TTC GCT GTC CAA
Arg Pro Pro Arg Trp Leu Glu Ile Phe Ala Val Gln
1090            1100            1110           1120
   CAG TTT GAA GAG AAA TCT TAC CAA AAC TTC ACA
   Gln Phe Glu Glu Lys Ser Tyr Gln Asn Phe Thr
            1130            1140           1150
GTG AGG GCG ATC GAC GGA GAC ACT GAG ATC AAT ATG
Val Arg Ala Ile Asp Gly Asp Thr Glu Ile Asn Met
  1160            1170           1180            1190
CCT ATC AAC TAC AGG CTG ATC ACA AAT GAG GAA GAC
Pro Ile Asn Tyr Arg Leu Ile Thr Asn Glu Glu Asp
          1200            1210           1220
ACA TTC TTC AGC ATT GAG GCC CTG CCT GGT GGA AAA
Thr Phe Phe Ser Ile Glu Ala Leu Pro Gly Gly Lys
1230             1240           1250            1260
   AGC GGG GCT GTA TTC CTC GTG TCG CCA ATT GAC
   Ser Gly Ala Val Phe Leu Val Ser Pro Ile Asp
            1270            1280           1290
CGC GAC ACA CTG CAA CGA GAG GTG TTT CCA CTT ACG
Arg Asp Thr Leu Gln Arg Glu Val Phe Pro Leu Thr
1300             1310           1320            1330
   ATC GTC GCT TAC AAA TAT GAT GAG GAG GCC TTC TCC
   Ile Val Ala Tyr Lys Tyr Asp Glu Glu Ala Phe Ser
            1340            1350           1360
ACA TCA ACA AAC GTG GTC ATC ATT GTG ACA GAC ATC
Thr Ser Thr Asn Val Val Ile Ile Val Thr Asp Ile
```

FIG. 1C

```
        1370                1380                1390                1400
           AAC GAC CAA AGA CCT GAA CCT ATA CAC AAG GAA
           Asn Asp Gln Arg Pro Glu Pro Ile His Lys Glu
              1410                1420                1430
    TAT CGA CTG GCA ATC ATG GAG GAG ACG CCC CTG ACC
    Tyr Arg Leu Ala Ile Met Glu Glu Thr Pro Leu Thr
    1440                1450                1460                1470
       CTC AAC TTC GAT AAA GAA TTC GGA TTT CAT GAT
       Leu Asn Phe Asp Lys Glu Phe Gly Phe His Asp
              1480                1490                1500
    AAG GAT TTA GGT CAA AAC GCT CAG TAC ACG GTG CGT
    Lys Asp Leu Gly Gln Asn Ala Gln Tyr Thr Val Arg
    1510                1520                1530                1540
        CTA GAG AGC GTG GAC CCT CCA GGC GCT GCT GAG GCA
        Leu Glu Ser Val Asp Pro Pro Gly Ala Ala Glu Ala
              1550                1560                1570
    TTC TAC ATA GCG CCT GAA GTC GGC TAC CAG CGA CAG
    Phe Tyr Ile Ala Pro Glu Val Gly Tyr Gln Arg Gln
    1580                1590                1600                1610
         ACC TTC ATC ATG GGC ACC CTC AAT CAC TCC ATG
         Thr Phe Ile Met Gly Thr Leu Asn His Ser Met
              1620                1630                1640
    CTG GAT TAC GAA GTG CCA GAG TTT CAG AGT ATT ACG
    Leu Asp Tyr Glu Val Pro Glu Phe Gln Ser Ile Thr
    1650                1660                1670                1680
        ATT CGG GTG GTA GCG ACC GAC AAC AAC GAC ACG
        Ile Arg Val Val Ala Thr Asp Asn Asn Asp Thr
               1690                1700                1710
    AGG CAC GTG GGC GTC GCG TTG GTT CAC ATT GAC CTC
    Arg His Val Gly Val Ala Leu Val His Ile Asp Leu
    1720                1730                1740                1750
        ATC AAT TGG AAC GAT GAG CAG CCG ATC TTC GAA CAC
        Ile Asn Trp Asn Asp Glu Gln Pro Ile Phe Glu His
              1760                1770                1780
    GCC GTG CAG ACC GTC ACC TTC GAC GAG ACT GAA GGC
    Ala Val Gln Thr Val Thr Phe Asp Glu Thr Glu Gly
```

FIG. 1D

```
         1790          1800          1810          1820
     GAG GGG TTC TTC GTC GCC AAG GCG GTT GCA CAC
     Glu Gly Phe Phe Val Ala Lys Ala Val Ala His
         1830          1840          1850
GAC AGA GAC ATC GGG GAT GTC GTC GAG CAT ACT TTA
Asp Arg Asp Ile Gly Asp Val Val Glu His Thr Leu
     1860          1870          1880          1890
    TTG GGT AAC GCT GTT AAC TTC CTG ACC ATC GAC
    Leu Gly Asn Ala Val Asn Phe Leu Thr Ile Asp
         1900          1910          1920
AAA CTC ACC GGC GAC ATC CGC GTC TCA GCT AAC GAC
Lys Leu Thr Gly Asp Ile Arg Val Ser Ala Asn Asp
     1930          1940          1950          1960
   TCC TTC AAC TAC CAT CGA GAA AGT GAA TTA TTT GTG
   Ser Phe Asn Tyr His Arg Glu Ser Glu Leu Phe Val
         1970          1980          1990
CAG GTG CGA GCT ACA GAC ACG CTG GGC GAA CCC TTC
Gln Val Arg Ala Thr Asp Thr Leu Gly Glu Pro Phe
     2000          2010          2020          2030
     CAC ACG GCG ACG TCA CAG CTG GTC ATA CGA CTA
     His Thr Ala Thr Ser Gln Leu Val Ile Arg Leu
         2040          2050          2060
AAT GAC ATC AAC AAC ACG CCA CCC ACC TTA CGG CTG
Asn Asp Ile Asn Asn Thr Pro Pro Thr Leu Arg Leu
     2070          2080          2090          2100
    CCT CGA GGC AGT CCC CAA GTG GAG GAG AAC GTG
    Pro Arg Gly Ser Pro Gln Val Glu Glu Asn Val
         2110          2120          2130
CCT GAT GGC CAC GTC ATC ACC CAG GAG TTA CGC GCC
Pro Asp Gly His Val Ile Thr Gln Glu Leu Arg Ala
     2140          2150          2160          2170
   ACC GAC CCC GAC ACC ACG GCC GAT CTG CGC TTC GAG
   Thr Asp Pro Asp Thr Thr Ala Asp Leu Arg Phe Glu
         2180          2190          2200
ATA AAC TGG GAC ACC TCT TTC GCC ACC AAG CAA GGC
Ile Asn Trp Asp Thr Ser Phe Ala Thr Lys Gln Gly
```

FIG. 1E

```
       2210         2220         2230         2240
    CGC CAG GCT AAC CCC GAC GAG TTT AGG AAT TGC
    Arg Gln Ala Asn Pro Asp Glu Phe Arg Asn Cys
         2250         2260         2270
GTG GAA ATC GAG ACC ATC TTC CCC GAG ATT AAC AAC
Val Glu Ile Glu Thr Ile Phe Pro Glu Ile Asn Asn
2280         2290         2300         2310
    CGG GGA CTG GCT ATC GGC CGC GTT GTA GCG CGC
    Arg Gly Leu Ala Ile Gly Arg Val Val Ala Arg
         2320         2330         2340
GAA ATC AGA CAC AAC GTG ACC ATA GAC TAC GAG GAG
Glu Ile Arg His Asn Val Thr Ile Asp Tyr Glu Glu
2350         2360         2370         2380
  TTT GAG GTC CTC TCC CTC ACA GTG AGG GTG CGT GAC
  Phe Glu Val Leu Ser Leu Thr Val Arg Val Arg Asp
         2390         2400         2410
CTT AAC ACC GTC TAC GGA GAC GAC TAC GAC GAA TCG
Leu Asn Thr Val Tyr Gly Asp Asp Tyr Asp Glu Ser
2420         2430         2440         2450
    ATG CTC ACA ATA ACT ATA ATC GAT ATG AAC GAC
    Met Leu Thr Ile Thr Ile Ile Asp Met Asn Asp
         2460         2470         2480
AAC GCG CCG GTG TGG GTG GAG GGG ACT CTG GAG CAG
Asn Ala Pro Val Trp Val Glu Gly Thr Leu Glu Gln
2490         2500         2510         2520
   AAC TTC CGA GTC CGC GAG ATG TCG GCG GGC GGG
   Asn Phe Arg Val Arg Glu Met Ser Ala Gly Gly
         2530         2540         2550
CTC GTG GTG GGC TCC GTG CGC GCG GAC GAC ATC GAC
Leu Val Val Gly Ser Val Arg Ala Asp Asp Ile Asp
2560         2570         2580         2590
   GGA CCG CTC TAC AAC CAA GTG CGA TAC ACC ATT TTC
   Gly Pro Leu Tyr Asn Gln Val Arg Tyr Thr Ile Phe
         2600         2610         2620
CCT CGT GAA GAC ACA GAT AAG GAC CTG ATA ATG ATC
Pro Arg Glu Asp Thr Asp Lys Asp Leu Ile Met Ile
```

FIG. 1F

```
         2630              2640              2650              2660
       GAC TTC CTC ACG GGT CAA ATT TCC GTG AAC ACA
       Asp Phe Leu Thr Gly Gln Ile Ser Val Asn Thr
             2670              2680              2690
    AGC GGC GCC ATC GAC GCG GAT ACT CCT CCA CGC TTC
    Ser Gly Ala Ile Asp Ala Asp Thr Pro Pro Arg Phe
    2700              2710              2720              2730
       CAC CTC TAC TAT ACA GTG GTC GCT AGT GAC CGA
       His Leu Tyr Tyr Thr Val Val Ala Ser Asp Arg
             2740              2750              2760
    TGC TCG ACA GAA GAT CCT GCA GAT TGC CCC CCT GAC
    Cys Ser Thr Glu Asp Pro Ala Asp Cys Pro Pro Asp
    2770              2780              2790              2800
     CCG ACT TAT TGG GAA ACC GAA GGA AAT ATC ACA ATC
     Pro Thr Tyr Trp Glu Thr Glu Gly Asn Ile Thr Ile
             2810              2820              2830
    CAC ATC ACC GAC ACG AAC AAC AAG GTC CCG CAG GCG
    His Ile Thr Asp Thr Asn Asn Lys Val Pro Gln Ala
    2840              2850              2860              2870
       GAA ACG ACT AAG TTC GAT ACC GTC GTG TAT ATT
       Glu Thr Thr Lys Phe Asp Thr Val Val Tyr Ile
             2880              2890              2900
    TAC GAG AAC GCA ACC CAC TTA GAC GAG GTG GTC ACT
    Tyr Glu Asn Ala Thr His Leu Asp Glu Val Val Thr
    2910              2920              2930              2940
       CTG ATA GCC AGT GAT CTT GAC AGA GAC GAA ATA
       Leu Ile Ala Ser Asp Leu Asp Arg Asp Glu Ile
             2950              2960              2970
    TAC CAC ACG GTG AGC TAC GTC ATC AAT TAT GCA GTG
    Tyr His Thr Val Ser Tyr Val Ile Asn Tyr Ala Val
    2980              2990              3000              3010
      AAC CCT CGA CTG ATG AAC TTC TTC TCC GTG AAC CGA
      Asn Pro Arg Leu Met Asn Phe Phe Ser Val Asn Arg
             3020              3030              3040
    GAG ACC GGC CTG GTG TAC GTG GAC TAT GAG ACC CAG
    Glu Thr Gly Leu Val Tyr Val Asp Tyr Glu Thr Gln
```

FIG. 1G

```
         3050         3060           3070           3080
     GGT AGT GGC GAG GTG CTG GAC CGT GAT GGT GAT
     Gly Ser Gly Glu Val Leu Asp Arg Asp Gly Asp
        3090         3100          3110
GAA CCA ACG CAC CGT ATC TTC TTC AAC CTC ATC GAC
Glu Pro Thr His Arg Ile Phe Phe Asn Leu Ile Asp
3120          3130          3140          3150
    AAC TTC ATG GGG GAA GGA GAA GGT AAC AGA AAT
    Asn Phe Met Gly Glu Gly Glu Gly Asn Arg Asn
         3160          3170         3180
CAG AAC GAC ACA GAA GTT CTC GTT ATC TTG TTG GAT
Gln Asn Asp Thr Glu Val Leu Val Ile Leu Leu Asp
3190         3200           3210          3220
  GTG AAT GAC AAT GCT CCT GAA TTG CCA CCG CCG AGC
  Val Asn Asp Asn Ala Pro Glu Leu Pro Pro Pro Ser
        3230          3240         3250
GAA CTC TCT TGG ACT ATA TCT GAG AAC CTT AAG CAG
Glu Leu Ser Trp Thr Ile Ser Glu Asn Leu Lys Gln
3260          3270          3280          3290
      GGC GTC CGT CTT GAA CCA CAT ATC TTC GCC CCG
      Gly Val Arg Leu Glu Pro His Ile Phe Ala Pro
         3300          3310          3320
GAC CGC GAC GAG CCC GAC ACA GAC AAC TCC AGG GTC
Asp Arg Asp Glu Pro Asp Thr Asp Asn Ser Arg Val
3330         3340          3350          3360
    GGC TAC GAG ATC CTG AAC CTC AGC ACG GAG CGG
    Gly Tyr Glu Ile Leu Asn Leu Ser Thr Glu Arg
         3370         3380          3390
GAC ATC GAA GTG CCG GAG CTG TTT GTG ATG ATA CAG
Asp Ile Glu Val Pro Glu Leu Phe Val Met Ile Gln
3400          3410          3420          3430
   ATC GCG AAC GTC ACG GGA GAG CTG GAG ACC GCC ATG
   Ile Ala Asn Val Thr Gly Glu Leu Glu Thr Ala Met
         3440         3450          3460
    GAC CTC AAG GGA TAT TGG GGG ACG TAC GCT ATA CAT
    Asp Leu Lys Gly Tyr Trp Gly Thr Tyr Ala Ile His
```

*FIG. 1H*

```
         3470           3480           3490           3500
     ATA CGG GCA TTC GAC CAC GGC ATT CCG CAA ATG
     Ile Arg Ala Phe Asp His Gly Ile Pro Gln Met
         3510           3520           3530
 TCC ATG AAC GAG ACA TAT GAG CTG ATC ATC CAT CCG
 Ser Met Asn Glu Thr Tyr Glu Leu Ile Ile His Pro
 3540           3550           3560           3570
      TTC AAC TAC TAC GCG CCT GAG TTC GTC TTC CCG
      Phe Asn Tyr Tyr Ala Pro Glu Phe Val Phe Pro
            3580           3590           3600
 ACC AAC GAT GCC GTC ATA CGA CTT GCG AGG GAA CGA
 Thr Asn Asp Ala Val Ile Arg Leu Ala Arg Glu Arg
 3610           3620           3630           3640
   GCT GTA ATC AAT GGA GTT CTA GCG ACA GTG AAC GGA
   Ala Val Ile Asn Gly Val Leu Ala Thr Val Asn Gly
         3650           3660           3670
 GAG TTC TTG GAG CGG ATA TCG GCG ACT GAT CCG GAC
 Glu Phe Leu Glu Arg Ile Ser Ala Thr Asp Pro Asp
 3680           3690           3700           3710
       GGA CTC CAC GCG GGC GTC GTC ACC TTC CAA GTG
       Gly Leu His Ala Gly Val Val Thr Phe Gln Val
            3720           3730           3740
 GTA GGC GAT GAG GAA TCA CAA CGG TAC TTT CAA GTA
 Val Gly Asp Glu Glu Ser Gln Arg Tyr Phe Gln Val
 3750           3760           3770           3780
    GTT AAC GAT GGC GAG AAC CTC GGC TCG TTG AGG
    Val Asn Asp Gly Glu Asn Leu Gly Ser Leu Arg
         3790           3800           3810
 TTA CTG CAA GCC GTT CCA GAG GAG ATC AGG GAG TTC
 Leu Leu Gln Ala Val Pro Glu Glu Ile Arg Glu Phe
 3820           3830           3840           3850
  CGG ATA ACG ATT CGC GCT ACA GAC CAG GGA ACG GAC
  Arg Ile Thr Ile Arg Ala Thr Asp Gln Gly Thr Asp
         3860           3870           3880
 CCA GGA CCG CTG TCC ACG GAC ATG ACG TTC AGA GTT
 Pro Gly Pro Leu Ser Thr Asp Met Thr Phe Arg Val
```

FIG. 1I

```
3890              3900              3910              3920
   GTT TTT GTG CCC ACG CAA GGA GAA CCT AGA TTC
   Val Phe Val Pro Thr Gln Gly Glu Pro Arg Phe
      3930              3940              3950
GCG TCC TCA GAA CAT GCT GTC GCT TTC ATA GAA AAG
Ala Ser Ser Glu His Ala Val Ala Phe Ile Glu Lys
3960              3970              3980              3990
   AGT GCC GGC ATG GAA GAG TCT CAC CAA CTT CCT
   Ser Ala Gly Met Glu Glu Ser His Gln Leu Pro
         4000              4010              4020
CTA GCA CAA GAC ATC AAG AAC CAT CTC TGT GAA GAC
Leu Ala Gln Asp Ile Lys Asn His Leu Cys Glu Asp
4030              4040              4050              4060
 GAC TGT CAC AGC ATT TAC TAT CGT ATT ATC GAT GGC
 Asp Cys His Ser Ile Tyr Tyr Arg Ile Ile Asp Gly
       4070              4080              4090
AAC AGC GAA GGT CAT TTC GGC CTG GAT CCT GTT CGC
Asn Ser Glu Gly His Phe Gly Leu Asp Pro Val Arg
4100              4110              4120              4130
    AAC AGG TTG TTC CTG AAG AAA GAG CTG ATA AGG
    Asn Arg Leu Phe Leu Lys Lys Glu Leu Ile Arg
         4140              4150              4160
GAA CAA AGT GCC TCC CAC ACT CTG CAA GTG GCG GCT
Glu Gln Ser Ala Ser His Thr Leu Gln Val Ala Ala
4170              4180              4190              4200
   AGT AAC TCG CCC GAT GGT GGC ATT CCA CTT CCT
   Ser Asn Ser Pro Asp Gly Gly Ile Pro Leu Pro
         4210              4220              4230
GCT TCC ATC CTT ACT GTC ACT GTT ACC GTG AGG GAG
Ala Ser Ile Leu Thr Val Thr Val Thr Val Arg Glu
4240              4250              4260              4270
  GCA GAC CCT CGT CCA GTG TTT GTG AGG GAA TTG TAC
  Ala Asp Pro Arg Pro Val Phe Val Arg Glu Leu Tyr
         4280              4290              4300
ACC GCA GGG ATA TCC ACA GCG GAC TCC ATC GGC AGA
Thr Ala Gly Ile Ser Thr Ala Asp Ser Ile Gly Arg
```

FIG. 1J

```
      4310         4320         4330         4340
    GAG CTG CTC AGA TTA CAT GCG ACC CAG TCT GAA
    Glu Leu Leu Arg Leu His Ala Thr Gln Ser Glu
        4350         4360         4370
GGC TCG GCC ATT ACT TAT GCT ATA GAC TAC GAT ACA
Gly Ser Ala Ile Thr Tyr Ala Ile Asp Tyr Asp Thr
4380         4390         4400         4410
    ATG GTA GTG GAC CCC AGC CTG GAG GCA GTG AGA
    Met Val Val Asp Pro Ser Leu Glu Ala Val Arg
         4420         4430         4440
CAG TCG GCT TTC GTA CTG AAC GCT CAA ACC GGA GTG
Gln Ser Ala Phe Val Leu Asn Ala Gln Thr Gly Val
4450         4460         4470         4480
 CTG ACG CTT AAT ATC CAG CCC ACG GCC ACG ATG CAT
 Leu Thr Leu Asn Ile Gln Pro Thr Ala Thr Met His
       4490         4500         4510
GGA CTG TTC AAA TTC GAA GTC ACA GCT ACT GAC ACG
Gly Leu Phe Lys Phe Glu Val Thr Ala Thr Asp Thr
4520         4530         4540         4550
    GCC GGC GCT CAG GAC CGC ACC GAC GTC ACC GTG
    Ala Gly Ala Gln Asp Arg Thr Asp Val Thr Val
         4560         4570         4580
TAC GTG GTA TCC TCG CAG AAC CGC GTC TAC TTC GTG
Tyr Val Val Ser Ser Gln Asn Arg Val Tyr Phe Val
4590         4600         4610         4620
    TTC GTC AAC ACG CTG CAA CAG GTC GAA GAC AAC
    Phe Val Asn Thr Leu Gln Gln Val Glu Asp Asn
         4630         4640         4650
AGA GAC TTT ATC GCG GAC ACC TTC AGC GCT GGG TTC
Arg Asp Phe Ile Ala Asp Thr Phe Ser Ala Gly Phe
4660         4670         4680         4690
 AAC ATG ACC TGC AAC ATC GAC CAA GTG GTG CCC GCT
 Asn Met Thr Cys Asn Ile Asp Gln Val Val Pro Ala
       4700         4710         4720
AAC GAC CCC GTC ACC GGC GTG GCG CTG GAG CAC AGC
Asn Asp Pro Val Thr Gly Val Ala Leu Glu His Ser
```

FIG. 1K

```
4730            4740            4750            4760
   ACG CAG ATG CGC GGC CAC TTC ATA CGG GAC AAC
   Thr Gln Met Arg Gly His Phe Ile Arg Asp Asn
       4770            4780            4790
GTA CCC GTA CTC GCT GAT GAG ATA GAA CAG ATC CGT
Val Pro Val Leu Ala Asp Glu Ile Glu Gln Ile Arg
4800            4810            4820            4830
   AGT GAC CTA GTC CTC CTG AGC TCG ATA CAA ACA
   Ser Asp Leu Val Leu Leu Ser Ser Ile Gln Thr
            4840            4850            4860
ACG CTG GCG GCG CGA TCG CTG GTG TTG CAG GAC TTG
Thr Leu Ala Ala Arg Ser Leu Val Leu Gln Asp Leu
4870            4880            4890            4900
   TTG ACC AAC TCC AGC CCG GAC TCG GCG CCT GAC TCG
   Leu Thr Asn Ser Ser Pro Asp Ser Ala Pro Asp Ser
            4910            4920            4930
AGC CTC ACG GTG TAC GTG CTG GCC TCA CTG TCT GCT
Ser Leu Thr Val Try Val Leu Ala Ser Leu Ser Ala
4940            4950            4960            4970
    GTG CTC GGT TTC ATG TGC CTT GTG CTA CTG CTT
    Val Leu Gly Phe Met Cys Leu Val Leu Leu Leu
        4980            4990            5000
ACC TTC ATC ATC AGG ACT AGA GCG CTA AAC CGA CGG
Thr Phe Ile Ile Arg Thr Arg Ala Leu Asn Arg Arg
5010            5020            5030            5040
   TTG GAA GCC CTG TCG ATG ACG AAG TAC GGC TCA
   Leu Glu Ala Leu Ser Met Thr Lys Tyr Gly Ser
           5050            5060            5070
CTG GAC TCT GGA TTG AAC CGC GCC GGC ATC GCC GCC
Leu Asp Ser Gly Leu Asn Arg Ala Gly Ile Ala Ala
5080            5090            5100            5110
   CCC GGC ACC AAC AAA CAC ACT GTG GAA GGC TCC AAC
   Pro Gly Thr Asn Lys His Thr Val Glu Gly Ser Asn
            5120            5130            5140
CCT ATC TTC AAT GAA GCA ATA AAG ACG CCA GAT TTA
Pro Ile Phe Asn Glu Ala Ile Lys Thr Pro Asp Leu
```

FIG. 1L

```
      5150          5160          5170          5180
   GAT GCC ATT AGC GAG GGT TCC AAC GAC TCT GAT
   Asp Ala Ile Ser Glu Gly Ser Asn Asp Ser Asp
        5190          5200          5210
CTG ATC GGC ATC GAA GAT CTT CCG CAC TTT GGC AAC
Leu Ile Gly Ile Glu Asp Leu Pro His Phe Gly Asn
5220          5230          5240          5250
   GTC TTC ATG GAT CCT GAG GTG AAC GAA AAG GCA
   Val Phe Met Asp Pro Glu Val Asn Glu Lys Ala
        5260          5270          5280
AAT GGT TAT CCC GAA GTC GCA AAC CAC AAC AAC AAC
Asn Gly Tyr Pro Glu Val Ala Asn His Asn Asn Asn
5290          5300          5310          5320
  TTC GCT TTC AAC CCG ACT CCC TTC TCG CCT GAG TTC
  Phe Ala Phe Asn Pro Thr Pro Phe Ser Pro Glu Phe
        5330          5340          5350          5360
GTT AAC GGA CAG TTC AGA AAG ATC TAGAAGATAACAACA
Val Asn Gly Gln Phe Arg Lys Ile
        5370          5380          5390          5400          5410
CTAGTTAAGATCATTAATTTTGGAGTTTGGAATTAAGATTTTTGAAAG
        5420          5430          5440          5450
GATAGTTGTGATAAGCCTGTGATTTTTAAAACTGTAATTGAAAAAA
5460          5470          5480          5490          5500
AAAATTGAGACCTCCATTTAAGCTCTTGCTCTCATCTCATCAAATTTT
   5510          5520          5530          5540          5550
ATAAAATGCCATTAGTCATTAAGATACTCGATTTAATTTAAGATTATT
      5560          5570          5580
TAAGATATTATGTAAAATAAATATATTGTC
```

*FIG. 1M*

SEQ ID NO. 2

| | | | | | | | | | |
|---|---|---|---|---|---|---|---|---|---|
| Met 1 | Ala | Val | Asp | Val 5 | Arg | Ile | Ala | Ala | Phe | Leu 10 | Leu |
| Val | Phe | Ile 15 | Ala | Pro | Ala | Val | Leu 20 | Ala | Gln | Glu | Arg |
| Cys 25 | Gly | Tyr | Met | Thr 30 | Ala | Ile | Pro | Arg | Leu | Pro 35 | Arg |
| Pro | Asp | Asn | Leu 40 | Pro | Val | Leu | Asn | Phe 45 | Glu | Gly | Gln |
| Thr | Trp 50 | Ser | Gln | Arg | Pro | Leu 55 | Leu | Pro | Ala | Pro | Glu 60 |
| Arg | Asp | Asp | Leu | Cys 65 | Met | Asp | Ala | Tyr | His 70 | Val | Ile |
| Thr | Ala | Asn 75 | Leu | Gly | Thr | Gln | Val | Ile 80 | Tyr | Met | Asp |
| Glu 85 | Glu | Ile | Glu | Asp | Glu 90 | Ile | Thr | Ile | Ala | Ile 95 | Leu |
| Asn | Tyr | Asn | Gly 100 | Pro | Ser | Thr | Pro | Phe 105 | Ile | Glu | Leu |
| Pro | Phe 110 | Leu | Ser | Gly | Ser | Tyr 115 | Asn | Leu | Leu | Met | Pro 120 |
| Val | Ile | Arg | Arg | Val 125 | Asp | Asn | Gly | Glu | Trp 130 | His | Leu |
| Ile | Ile | Thr 135 | Gln | Arg | Gln | His | Tyr 140 | Glu | Leu | Pro | Gly |
| Met 145 | Gln | Gln | Tyr | Met | Phe 150 | Asn | Val | Arg | Val | Asp 155 | Gly |
| Gln | Ser | Leu | Val 160 | Ala | Gly | Val | Ser | Leu 165 | Ala | Ile | Val |
| Asn | Ile 170 | Asp | Asp | Asn | Ala | Pro 175 | Ile | Ile | Gln | Asn | Phe 180 |
| Glu | Pro | Cys | Arg | Val 185 | Pro | Glu | Leu | Gly | Glu 190 | Pro | Gly |
| Leu | Thr | Glu | Cys 195 | Thr | Tyr | Gln | Val | Ser 200 | Asp | Ala | Asp |
| Gly | Arg | Ile | Ser | Thr | Glu 210 | Phe | Met | Thr | Phr | Arg 215 | Ile |

Annotations in sequence:
- CAD1 marker at position 60, with arrow starting from Arg-Asp at position 61
- CAD2 marker at position 165, with arrow extending from Ile

FIG. 2A

```
Asp Ser Val Arg Gly Asp Glu Glu Thr Phe Tyr Ile
            220                 225
Glu Arg Thr Asn Ile Pro Asn Gln Trp Met Trp Leu
        230             235                 240
Asn Met Thr Ile Gly Val Asn Thr Ser Leu Asn Phe
                245                 250
Val Thr Ser Pro Leu His Ile Phe Ser Val Thr Ala
            255             260
Leu Asp Ser Leu Pro Asn Thr His Thr Val Thr Met
265                 270                 275
Met Val Gln Val Ala Asn Val Asn Ser Arg Pro Pro
            280                 285
        CAD3 →
Arg Trp Leu Glu Ile Phe Ala Val Gln Gln Phe Glu
    290             295                 300
Glu Lys Ser Tyr Gln Asn Phe Thr Val Arg Ala Ile
                305             310
Asp Gly Asp Thr Glu Ile Asn Met Pro Ile Asn Tyr
            315             320
Arg Leu Ile Thr Asn Glu Glu Asp Thr Phe Phe Ser
325                 330                 335
Ile Glu Ala Leu Pro Gly Gly Lys Ser Gly Ala Val
            340             345
Phe Leu Val Ser Pro Ile Asp Arg Asp Thr Leu Gln
        350             355                 360
Arg Glu Val Phe Pro Leu Thr Ile Val Ala Tyr Lys
                365                 370
Tyr Asp Glu Glu Ala Phe Ser Thr Ser Thr Asn Val
        375                 380
Val Ile Ile Val Thr Asp Ile Asn Asp Gln Arg Pro
385         CAD4 →      390                 395
Glu Pro Ile His Lys Glu Tyr Arg Leu Ala Ile Met
            400                 405
Glu Glu Thr Pro Leu Thr Leu Asn Phe Asp Lys Glu
    410                 415                 420
Phe Gly Phe His Asp Lys Asp Leu Gly Gln Asn Ala
            425                 430
```

FIG. 2B

```
Gln Tyr Thr Val Arg Leu Glu Ser Val Asp Pro Pro
        435                 440
Gly Ala Ala Glu Ala Phe Tyr Ile Ala Pro Glu Val
445                 450                 455
Gly Tyr Gln Arg Gln Thr Phe Ile Met Gly Thr Leu
            460                 465
Asn His Ser Met Leu Asp Tyr Glu Val Pro Glu Phe
        470                 475             480
Gln Ser Ile Thr Ile Arg Val Val Ala Thr Asp Asn
                485         CAD5    490
Asn Asp Thr Arg His Val Gly Val Ala Leu Val His
            495                 500
Ile Asp Leu Ile Asn Trp Asn Asp Glu Gln Pro Ile
505                 510                 515
Phe Glu His Ala Val Gln Thr Val Thr Phe Asp Glu
            520                 525
Thr Glu Gly Glu Gly Phe Phe Val Ala Lys Ala Val
        530                 535             540
Ala His Asp Arg Asp Ile Gly Asp Val Val Glu His
            545                 550
Thr Leu Leu Gly Asn Ala Val Asn Phe Leu Thr Ile
        555                 560
Asp Lys Leu Thr Gly Asp Ile Arg Val Ser Ala Asn
565             570              575
Asp Ser Phe Asn Tyr His Arg Glu Ser Glu Leu Phe
            580                 585
Val Gln Val Arg Ala Thr Asp Thr Leu Gly Glu Pro
        590                 595             600
Phe His Thr Ala Thr Ser Gln Leu Val Ile Arg Leu
                605                 610     CAD6
Asn Asp Ile Asn Asn Thr Pro Pro Thr Leu Arg Leu
→           615                 620
Pro Arg Gly Ser Pro Gln Val Glu Glu Asn Val Pro
625                 630                 635
Asp Gly His Val Ile Thr Gln Glu Leu Arg Ala Thr
            640                 645
```

FIG. 2C

```
Asp Pro Asp Thr Thr Ala Asp Leu Arg Phe Glu Ile
    650                 655                 660
Asn Trp Asp Thr Ser Phe Ala Thr Lys Gln Gly Arg
            665                     670
Gln Ala Asn Pro Asp Glu Phe Arg Asn Cys Val Glu
        675                 680
Ile Glu Thr Ile Phe Pro Glu Ile Asn Asn Arg Gly
685                 690                 695
Leu Ala Ile Gly Arg Val Val Ala Arg Glu Ile Arg
            700                 705
His Asn Val Thr Ile Asp Tyr Glu Glu Phe Glu Val
    710                 715                 720
Leu Ser Leu Thr Val Arg Val Arg Asp Leu Asn Thr
                725                 730
Val Tyr Gly Asp Asp Tyr Asp Glu Ser Met Leu Thr
        735                 740
Ile Thr Ile Ile Asp Met Asn Asp Asn Ala Pro Val
745                 750                 755 CAD7
Trp Val Glu Gly Thr Leu Glu Gln Asn Phe Arg Val
→           760                 765
Arg Glu Met Ser Ala Gly Gly Leu Val Val Gly Ser
    770                 775                 780
Val Arg Ala Asp Asp Ile Asp Gly Pro Leu Tyr Asn
            785                 790
Gln Val Arg Tyr Thr Ile Phe Pro Arg Glu Asp Thr
        795                 800
Asp Lys Asp Leu Ile Met Ile Asp Phe Leu Thr Gly
805                 810                 815
Gln Ile Ser Val Asn Thr Ser Gly Ala Ile Asp Ala
            820                 825
Asp Thr Pro Pro Arg Phe His Leu Tyr Tyr Thr Val
    830                 835                 840
Val Ala Ser Asp Arg Cys Ser Thr Glu Asp Pro Ala
            845                 850
Asp Cys Pro Pro Asp Pro Thr Tyr Trp Glu Thr Glu
        855                 860
```

FIG. 2D

```
Gly Asn Ile Thr Ile His Ile Thr Asp Thr Asn Asn
865             870                 875
               ┌CAD8─────▶
Lys Val Pro Gln Ala Glu Thr Thr Lys Phe Asp Thr
            880             885
Val Val Tyr Ile Tyr Glu Asn Ala Thr His Leu Asp
890             895                     900
Glu Val Val Thr Leu Ile Ala Ser Asp Leu Asp Arg
                905             910
Asp Glu Ile Tyr His Thr Val Ser Tyr Val Ile Asn
        915             920
Tyr Ala Val Asn Pro Arg Leu Met Asn Phe Phe Ser
925             930                 935
Val Asn Arg Glu Thr Gly Leu Val Tyr Val Asp Tyr
            940             945
Glu Thr Gln Gly Ser Gly Glu Val Leu Asp Arg Asp
    950             955                     960
Gly Asp Glu Pro Thr His Arg Ile Phe Phe Asn Leu
                965             970
Ile Asp Asn Phe Met Gly Glu Gly Glu Gly Asn Arg
        975             980
Asn Gln Asn Asp Thr Glu Val Leu Val Ile Leu Leu
985             990                     995
                                   ┌CAD9─────▶
Asp Val Asn Asp Asn Ala Pro Glu Leu Pro Pro Pro
            1000            1005
Ser Glu Leu Ser Trp Thr Ile Ser Glu Asn Leu Lys
    1010            1015                1020
Gln Gly Val Arg Leu Glu Pro His Ile Phe Ala Pro
                1025            1030
Asp Arg Asp Glu Pro Asp Thr Asp Asn Ser Arg Val
        1035            1040
Gly Tyr Glu Ile Leu Asn Leu Ser Thr Glu Arg Asp
1045            1050                    1055
Ile Glu Val Pro Glu Leu Phe Val Met Ile Gln Ile
            1060            1065
Ala Asn Val Thr Gly Glu Leu Glu Thr Ala Met Asp
    1070            1075                1080
```

FIG. 2E

```
Leu Lys Gly Tyr Trp Gly Thr Tyr Ala Ile His Ile
                    1085                1090
Arg Ala Phe Asp His Gly Ile Pro Gln Met Ser Met
            1095                1100
Asn Glu Thr Tyr Glu Leu Ile Ile His Pro Phe Asn
1105                 1110 CAD10         1115
Tyr Tyr Ala Pro Glu Phe  Val Phe Pro Thr Asn Asp
            1120             1125
Ala Val Ile Arg Leu Ala Arg Glu Arg Ala Val Ile
        1130            1135              1140
Asn Gly Val Leu Ala Thr Val Asn Gly Glu Phe Leu
                1145                1150
Glu Arg Ile Ser Ala Thr Asp Pro Asp Gly Leu His
            1155            1160
Ala Gly Val Val Thr Phe Gln Val Val Gly Asp Glu
1165                1170                 1175
Glu Ser Gln Arg Tyr Phe Gln Val Val Asn Asp Gly
            1180            1185
Glu Asn Leu Gly Ser Leu Arg Leu Leu Gln Ala Val
        1190            1195            1200
Pro Glu Glu Ile Arg Glu Phe Arg Ile Thr Ile Arg
                1205                1210
Ala Thr Asp Gln Gly Thr Asp Pro Gly Pro Leu Ser
            1215            1220
Thr Asp Met Thr Phe Arg Val Val Phe Val Pro Thr
1225                 1230 CAD11         1235
Gln Gly Glu Pro Arg Phe  Ala Ser Ser Glu His Ala
            1240             1245
Val Ala Phe Ile Glu Lys Ser Ala Gly Met Glu Glu
            1250            1255            1260
Ser His Gln Leu Pro Leu Ala Gln Asp Ile Lys Asn
                1265                1270
His Leu Cys Glu Asp Asp Cys His Ser Ile Tyr Tyr
            1275            1280
Arg Ile Ile Asp Gly Asn Ser Glu Gly His Phe Gly
1285                 1290                 1295
```

FIG. 2F

```
Leu Asp Pro Val Arg Asn Arg Leu Phe Leu Lys Lys
                1300                1305
Glu Leu Ile Arg Glu Gln Ser Ala Ser His Thr Leu
        1310            1315                1320
Gln Val Ala Ala Ser Asn Ser Pro Asp Gly Gly Ile
                1325            1330
Pro Leu Pro Ala Ser Ile Leu Thr Val Thr Val Thr
        1335                1340
Val Arg Glu Ala Asp Pro Arg Pro Val Phe Val Arg
1345                1350                1355
Glu Leu Tyr Thr Ala Gly Ile Ser Thr Ala Asp Ser
                1360            1365
Ile Gly Arg Glu Leu Leu Arg Leu His Ala Thr Gln
        1370            1375                1380
Ser Glu Gly Ser Ala Ile Thr Tyr Ala Ile Asp Tyr
                1385            1390
Asp Thr Met Val Val Asp Pro Ser Leu Glu Ala Val
            1395                1400
Arg Gln Ser Ala Phe Val Leu Asn Ala Gln Thr Gly
1405                1410                1415
Val Leu Thr Leu Asn Ile Gln Pro Thr Ala Thr Met
                1420                1425
His Gly Leu Phe Lys Phe Glu Val Thr Ala Thr Asp
        1430            1435                1440
Thr Ala Gly Ala Gln Asp Arg Thr Asp Val Thr Val
                1445                1450
Tyr Val Val Ser Ser Gln Asn Arg Val Tyr Phe Val
            1455            1460
Phe Val Asn Thr Leu Gln Gln Val Glu Asp Asn Arg
1465                1470                1475
Asp Phe Ile Ala Asp Thr Phe Ser Ala Gly Phe Asn
                1480            1485
Met Thr Cys Asn Ile Asp Gln Val Val Pro Ala Asn
        1490            1495                1500
Asp Pro Val Thr Gly Val Ala Leu Glu His Ser Thr
                1505                1510
```

FIG. 2G

```
Gln Met Arg Gly His Phe Ile Arg Asp Asn Val Pro
        1515                    1520
Val Leu Ala Asp Glu Ile Glu Gln Ile Arg Ser Asp
1525                1530                    1535
Leu Val Leu Leu Ser Ler Ile Gln Thr Thr Leu Ala
            1540                1545
Ala Arg Ser Leu Val Leu Gln Asp Leu Leu Thr Asn
        1550                1555                1560
Ser Ser Pro Asp Ser Ala Pro Asp Ser Ser Leu Thr
                1565                1570
Val Thr Val Leu Ala Ser Leu Ser Ala Val Leu Gly
        1575                    1580
Phe Met Cys Leu Val Leu Leu Leu Thr Phe Ile Ile
1585                1590                    1595
Arg Thr Arg Ala Leu Asn Arg Arg Leu Glu Ala Leu
            1600                1605
Ser Met Thr Lys Tyr Gly Ser Leu Asp Ser Gly Leu
        1610                1615                1620
Asn Arg Ala Gly Ile Ala Ala Pro Gly Thr Asn Lys
                1625                1630
His Thr Val Glu Gly Ser Asn Pro Ile Phe Asn Glu
            1635                1640
Ala Ile Lys Thr Pro Asp Leu Asp Ala Ile Ser Glu
1645                    1650                1655
Gly Ser Asn Asp Ser Asp Leu Ile Gly Ile Glu Asp
                1660                    1665
Leu Pro His Phe Gly Asn Val Phe Met Asp Pro Glu
        1670                1675            1680
Val Asn Glu Lys Ala Asn Gly Tyr Pro Glu Val Ala
                1685                    1690
Asn His Asn Asn Asn Phe Ala Phe Asn Pro Thr Pro
            1695                1700
Phe Ser Pro Glu Phe Val Asn Gly Gln Phe Arg Lys
1705                    1710                1715

Ile
```

FIG. 2H

```
mP_EC1       EWVMPPIFVP----- ENGK----------- ----------------KSNK DRGTKIFYYSITGPGADSPPEGVFTIEKES-------
fat_EC18     EDTVYSFDID----- ENAQR---------- ----------------ARDADLGQNAQLSYGVVSDWANDVFSLNPQT-------
pC42_EC2     ASPVITLAIP----- ENTN T---------- ----------------ASDRDANELQVAEDQEEKQPQLIVM------------
HPT-1_EC1    IVTENIWKAPKPV-- EMVEN---------- ----------------VRWNDPGAQYSLVDKEKLPRFPFSIDQE-----------
BTRcad-1     ITANLGTQVIYMDEE IEDEITIAILNYNG PSTP---------------FIEELPFLSGSYNLLMPVIRRVDN-----------
BTRcad-2     QNFEPCRVP------ ELGEP---------- ----------------VSDADGRISTEFMTFRIDSVR----------------
BTRcad-3     LEIFAVQQFE----- EKSYQ---------- ----------------AIDGDTEINMPINYRLITNEEDTFFSIEALPGGKS-7
BTRcad-4     IHKEYRLAIM----- EETPL-TLNFDKEFG ----------------FHDKDLGQNAQYTVRLESVDPPGAAEAFYIAPEV----
BTRcad-5     EHAVQTVTFD----- ETRGE---------- ----------------AHDRDIGDVVEHTLLGNAVNFLTIDKLT----------
BTRcad-6     RLPRGSPQVE----- ENVPD---------- ----------------AIDPDITADLRFEINWDTSFATKQGRQANPDEFRNCVEIETIP
BTRcad-7     VEGTLEQNFRVR--- EMSAG---------- ----------------ADDIDGPLYNQVRYTIFPREDTDKDLIMIELPH--------
BTRcad-8     ETTKFDTVVYIY--- ENATH---------- ----------------ADDLDRDEIYHMVSYVINYAVNPRLMNFFSVNRET-----
BTRcad-9     PPPSELSWTIS---- ENLKQ---------- ----------------APDRDEPDTDNSRVGVETDIEVPELFVMIQIIANVT
BTRcad-10    VFPTNDAVIRLAR-- ERAVIN--------- ----------------GVLATVNGEFLERISAIDPDGLHAGVVTFQVVGDEESQRYFQVVDND----
BTRcad-11    ASSEHAVAFI----- EKSA----------- ----------------AQDIKNHLCEDDCHSIYYRIIDGNSEGHF-----------

Cadherin Consensus Motif  ------E........  -------G........  ----------------..........A.D.D.........

mP_EC1       GWLLLHMP------- --------------- LDREKIVKYELYGHAVSENGA------- SVEEPMNISIIVTDQNDNKPKF (SEQ ID NO:8)
fat_EC18     GMLTLTAR------- --------------- LDYEEVQHYILIVQAQDNGQP------- SLSTTITVYCNVLDLNDNAPIF (SEQ ID NO:9)
pC42_EC2     GN------------- --------------- LDRERWDSYDLTIKVQDGGSP------- PRATSALLRVTVLDTNDNAPKE (SEQ ID NO:10)
HPT-1_EC1    GDIYVTOP------- --------------- IDREEKDAYVFYAVAKDEYGK------- PLSYPLEIHVKVKDINDNPPT (SEQ ID NO:11)
BTRcad-1     GSASHH--------- --------------- HARQHYELPGMQQYMFNVRVD------- GQSLVAGVSLAIVNIIDDNAPIL
BTRcad-2     GDEETFYIERTNIPNQWMWLNMTIGVNT   SLNFVTSPLHIFSVTALDSL-------- PNTHTVTMMVQVANMNSRPPRW
BTRcad-3     GAVFLV--------- --------------- IDRDTLQREVFPLTIVAYKYDEE----- AFSTSTNVVIIVTDIINDQRPEP
BTRcad-4     GYQRQTFIMGTLNHSM --------------- IDYEVPEFQSITIRVVATDNNDT----- RHVGVALVHIDLINWNDEQPIE
BTRcad-5     GDIRVSANDSFN--- --------------- YHRESELFVQVRATDTLGQP--------- FHTATSQLVIRLNDINNTPPI
BTRcad-6     -FPEINNINNRGLAIGRVVAKEIRHNVT    IDRDGDEPTHRIFFNLIDNFMGEGEGN- DDYDESMLTITIIDMNDNAPMW
BTRcad-7     GSNFRE-HKRRIDANTPPRFHLYYTVVAS   DRCSTEDPADCPPDPT------------ YWETEGNITIHITDINNKVPQA
BTRcad-8     GLVVYDYETQGSG-- --------------- EIREFRITIRATDQGTDP---------- GPLSTDMTFRVVFVPTQGEPRF
BTRcad-9     GYEILNLSTERDIEVPELFVMIQIANVT    EILETAMDLKGYWGTYAIYILAFDHGIPQMSMNETYELIIHPYYAPEF
BTRcad-10    GENLGSLRLLQAVPE --------------- LIRKDSASHTLQVAASNSPDGGI----- PLPASILTVTVTVREADPRPMF
BTRcad-11    GLDPVRNRLFLKKE-- ---------------

Cadherin Consensus Motif  G.............  ........DRE...........  ..........D.ND..P.F
```

FIG. 3

METHOD FOR SCREENING CANDIDATE PESTICIDES USING A RECEPTOR THAT BINDS *BACILLUS THURINGIENSIS* TOXIN

This application is a divisional of U.S. patent application Ser. No. 08/982,129 filed on Dec. 1, 1997, U.S. Pat. No. 6,007,981, which is a divisional of U.S. patent application Ser. No. 08/326,117 filed Oct. 19, 1994, U.S. Pat. No. 5,693,491.

ACKNOWLEDGEMENT OF GOVERNMENT SUPPORT

Work resulting in the present invention was supported in part by Research Agreement 58-319R-3-011 from the Office of International Cooperation and Development, U.S.D.A. and by Cooperative Agreement 58-5410-1-135 from the Arthropod-Borne Animal Disease Laboratory, Agricultural Research Service, U.S.D.A. and by Grant HD-18702 from the National Institutes of Health. The U.S. government has certain rights in this invention.

TECHNICAL FIELD

The invention relates to receptors that bind toxins from *Bacillus; thuringiensis* and thus to pesticides and pest resistance. More particularly, the invention concerns recombinantly produced receptors that bind BT toxin and to their use in assays for improved pesticides, as well as in mediation of cell and tissue destruction, dissociation, dispersion, cell-to-cell association, and changes in morphology.

BACKGROUND ART

It has long been recognized that the bacterium *Bacillus thuringiensis* (BT) produces bacteriocidal proteins that are toxic to a limited range of insects, mostly in the orders Lepidoptera, Coleoptera and Diptera. Advantage has been taken of these toxins in controlling pests, mostly by applying bacteria to plants or transforming plants themselves so that they generate the toxins by virtue of their transgenic character. The toxins themselves are glycoprotein products of the cry gene as described by Höfte, H. et al. *Microbiol Rev* (1989) 53:242. It has been established that the toxins function in the brush-border of the insect midgut epithelial cells as described by Gill, S. S. et al. *Annu Rev Entomol* (1992) 37:615. Specific binding of BT toxins to midgut brush border membrane vesicles has been reported by Hofmann, C. et al. *Proc Natl Acad Sci USA* (1988) 85:7844; Van Rie, J. et al. *Eur J Biochem* (1989) 186:239; and Van Rie, J. et al. *Appl Environ Michrobiol* (1990) 56:1378.

Presumably, the toxins generated by BT exert their effects by some kind of interaction with receptors in the midgut. The purification of a particular receptor from *Manduca sexta* was reported by the present inventors in an article by Vadlamudi, R. K. et al. *J Biol Chem* (1993) 268:12334. In this report, the receptor protein was isolated by immunoprecipitating toxin-binding protein complexes with toxin-specific antisera and separating the complexes by SDS-PAGE followed by electroelution. However, to date, there has been no structural information concerning any insect receptor which binds BT toxin, nor have, to applicants' knowledge, any genes encoding these receptors been recovered.

DISCLOSURE OF THE INVENTION

The invention provides recombinant materials for the production of BT toxin-binding receptors as well as methods to employ these materials to generate receptors for use in screening assays for candidate pesticides. Since the native cDNA sequence encoding this receptor, designated BT-$R_1$, has been retrieved-from the tobacco hornworm, encoding DNA for receptors in other species of insects, as well as in other organisms, which have homology to hornworm receptor can be obtained.

Thus, in one aspect, the invention is directed to a polynucleotide in purified and isolated form which comprises a nucleotide sequence encoding a receptor that binds a BT toxin and other ligands and which has the requisite homology to the BT-$R_1$ protein.

In other aspects, the invention is directed to expression systems for nucleotide sequences encoding the receptor, to methods of producing the receptor recombinantly, to the receptor as thus produced, to antibodies specifically immunoreactive with the receptor, to assay methods useful for screening candidate pesticides, to antisense polynucleotides corresponding to the coding sequence, to methods of targeting tissues and/or cells using the binding characteristics of the receptor, and to methods of manipulating tissues and/or cells using the function of the receptor.

BRIEF DESCRIPTION OF THE DRAWINGS

FIGS. 1A–1M (SEQ ID NO:1 and SEQ ID NO:2) show the nucleotide sequence and deduced amino acid sequence of cDNA encoding the BT-$R_1$ protein from *M. sexta*.

FIGS. 2A–2H (SEQ ID NO:2) show the amino acid sequence of BT-$R_1$ protein from *M. sexta*.

FIG. 3 (SEQ ID NO:8–11) shows a comparison of amino acid sequences from BT-$R_1$ (SEQ ID NO:2) to the sequences of other cadherins.

MODE OF CARRYING OUT THE INVENTION

The invention provides, for the first time, sequence information concerning receptors that bind BT toxins in insect midguts.

The BT-$R_1$ cDNA clone retrieved as described in the examples below encodes a protein having an identical amino acid composition with that described for the native receptor. Furthermore, toxin-binding specificity and immunoreactivity are similar. The native 210 kD BT-$R_1$ specifically recognizes cryIA(b) toxin of BT-berliner; a $K_d$ value of 708 pM was obtained for the native protein.

The cryIA(b) toxin selectively kills *M. sexta* larvae with an $LC_{50}$ of 7.5 ng/cm$^2$ of diet surface. BT-$R_1$ binds the toxin under both reducing and nonreducing conditions and pro-tease treatment of intestinal BBMV vesicles prepared from *M. sexta* showed that a 50 kD fragment of the 210 kD receptor is sufficient for toxin binding. The 50 kD toxin-binding domain is extracellular since the intestinal BBMV vesicles are oriented predominantly right side out as reported by Haase, W. H. et al. *Biochem* (1978) 172:57. This is consistent with the characteristics of the deduced amino acid sequence of the cDNA clone described below, as well as with the binding of toxin to the surface of intact BT-$R_1$ transfected human embryonic 293 cells as described in Example 3.

Whereas a particular cDNA clone from the tobacco hornworm has been described as illustration, the availability of this sequence information permits retrieval of corresponding receptors responsive to BT and related toxins from other species. This is conveniently accomplished by using the cDNA obtained in the present invention as a probe for screening cDNA or genomic libraries under conditions of stringency which eliminate false positives and retrieve substantially only corresponding receptors with coding sequences that are homologous to the coding sequence for the receptor of the present invention. Thus, the $BT-R_1$ protein itself and receptor proteins encoded by a nucleotide sequence homologous to the native nucleotide sequence encoding $BT-R_1$ are provided by the invention. Alternatively, PCR-mediated cloning can be used; however, this method does not take advantage of the detailed and complete information that resides in the availability of the nucleotide sequence encoding the full-length receptor from *M. sexta*. Also, PCR-mediated cloning introduces errors in natural DNA sequences. Thus, by using the full-length cDNA as a probe under conditions of appropriate stringency, only nucleotide sequences encoding the corresponding receptors will be obtained. The standard hybridization conditions include hybridization with nonspecific DNA such as salmon DNA at 50° C. and washing at 45° C. To obtain corresponding receptors having the lowest detectable homology with the receptor from *M. sexta*, the cDNA probe is hybridized under conditions of low standard stringency (30–37° C. and 4–6×SSC. More closely related corresponding receptors are obtained by hybridizing the cDNA probe under moderate standard stringency conditions (40–50° C. in 1×SSC). A clone containing the cDNA insert for use as a probe was deposited at the American Type Culture Collection as ATCC 98173.

The distribution of receptors of appropriate homology in the animal kingdom is believed to be fairly wide. Indeed, it is thought that higher organisms such as mammals, including primates, contain corresponding receptors which are homologous to $BT-R_1$ but respond to modified forms of BT toxins. In addition, other parasites such as nematodes, both those that afflict plants and those that afflict animals, will contain corresponding receptors.

Although one of the advantages of the use of BT toxins as insecticides is its specificity for certain orders of insects, this specificity is believed to result from the particular structure of the BT toxin rather than the unavailability of a corresponding mechanism in other insect orders. Thus, modified forms of BT toxin would be effective with respect to insects which contain homologous but slightly different forms of the receptor from that of the $BT-R_1$ protein illustrated below.

As used herein, "A receptor that specifically binds a BT toxin" refers to a receptor which is homologous to the $BT-R_1$ protein illustrated herein and which binds to either BT toxins themselves or to BT toxins that are sufficiently modified so as to bind these receptors which provide the required homology to $BT-R_1$.

The criteria for inclusion of a receptor in the present invention are the requirements that 1) it behave as a receptor —i.e., be capable of being displayed at the cell membrane; 2) it be sufficiently homologous to the $BT-R_1$ receptor described herein that a nucleotide sequence encoding the protein hybridizes under the stringency conditions described above to the nucleotide sequence encoding $BT-R_1$ as contained in the plasmid deposited at the American Type Culture Collection as ATCC 98173; and 3) when displayed on the surface of a cell, it is capable of binding a BT toxin or a modified form of BT toxin that exerts a cytotoxic effect either on the cell in which the receptor resides or in a tissue with which the cell is associated.

The structural characteristics of the "modified BT toxin" are defined by the functional property set forth above, but it may be convenient to design modified forms of BT toxin by conservative amino acid substitutions or other known protein-manipulating techniques applied to naturally occurring BT toxins.

The presence of similar receptors in noninsect organisms as well as other insects besides those harboring $BT-R_1$ is supported by the sequence similarity of the. $BT-R_1$ protein to that of the various members of the cadherin superfamily of proteins, which are membrane glycoproteins believed to mediate calcium-dependent cell aggregation and sorting. See, for example, Takeichi, M. *Science* (1991) 251:1451; and Takeichi, M. *N Rev Biochem* (1990) 59:237.

Included in this superfamily are desmoglien, desmocollins, the Drosophila fat tumor suppressor, human intestinal peptide transport protein and T-cadherin. All of these proteins share common extracellular motifs although their cytoplasmic domains differ. Goodwin, L. et al. *Biochem Biophys Res Commun* (1990) 173:1224; Holton, J. L. et al. *J Cell Sci* (1990) 97:239; Bestal, D. J. *J Cell Biol* (1992) 119:451; Mahoney, P. A. et al. *Cell* (1991) 853; Dantzig, A. H. et al. *Science* (1994) 264:430; and Sano, K. et al. *EMBO J* (1993) 12:2249. Inclusion of $BT-R_1$ in the cadherin superfamily is further supported by the report that EDTA decreases the binding of cryIA(b) toxin of BT to the 210 kD receptor of *M. sexta* (Martinez-Ramirez, A. C. et al. *Biochm Biophys Res Commun* (1994) 201:782).

It is noted below that the amino acid sequence of $BT-R_1$ reveals that a calcium-binding motif is present. This is consistent with the possibility that cells having, receptors to bind toxin may themselves survive although they render the tissues in which they are included permeable to solutes and thus effect disintegration of the tissue. Such a mechanism is proposed for the death of insects that ingest the toxin via the epithelial cells in their midgut by Knowles, B. H. et al. *Biochim Biophys Acta* (1987) 924:509. Such a mechanism is also supported in part by the results set forth in Example 4 hereinbelow which indicate that the effect of the toxin on embryonic 293cells modified to express the receptor at their surface is reversible.

Thus, in summary, the invention provides a family of receptors that is able to mediate the negative effects exerted by BT toxin or its modified forms on the cells expressing the receptor, by damaging the cells themselves and/or the tissue or organ of which the cells form a part. The receptor may be expressed natively at the surface of the target cells or the target cells may be modified to contain an expression system which will effect the display of receptor at the surface. The availability of this family of receptors and recombinant methods for its production and for the production of cells displaying it at their surfaces provides a number of opportunities to conduct screening assays for improved toxins, particularly insecticidal toxins, for generation of antibodies that can be useful as alternatives to chemotherapeutic agents for the destruction and/or dissociation of unwanted cells or tissues, and for the design of improved toxins and pharmaceuticals.

Screening Assays

The availability of the recombinant family of receptors of the present invention permits design of straightforward screening assays for toxins which will interact successfully with these receptors resulting in measurable effects on the cells in which the receptors reside. Briefly, suitable host cells, such as COS cells for transient expression, CHO cells for stable expression, and a variety of other mammalian and insect host cells can be modified to contain expression vectors appropriate to the hosts for the production of the receptors of the invention displayed on the surfaces of the cells. Since the receptors are natively membrane proteins, no particular design of the expression system is required in order to effect their disposition at the cell surface. Expression vectors suitable for any desired host are generally known in the art. For example, for mammalian expression, suitable control sequences include the SV40 and adenovirus promoters as constitutive promoters, the metallothionein inducible promoter, suitable enhancers, if desired, and termination signals and the like. For insect cells, the bacculovirus system is preferred. For other eucaryotic cells such as yeast, the glycolytic enzyme promoters and various amino acid synthesis promoters are commonly employed. Procaryotic cells such as E. coli also may be adapted for expression of the receptor in the assay of the invention, for instance by using a reporter gene under the control of cyclic AMP and operably linked to the receptor via protein G such that toxin binding will interrupt adenyl cyclase activity and thereby produce a detectable change in reporter gene activity. The assay system in a prokaryotic host may require further modification to compensate for lack of glycosylation which is known to occur in insect cells where the $BT-R_1$ protein is naturally expressed.

The cells are modified by transfection, retroviral infection, electroporation or other known means, to contain the desired expression system and then cultured under conditions wherein the receptor protein is produced and displayed. If desired, the cells are then recovered from the culture for use in the assay, or the culture itself can be used per se.

In the assays, the modified cells are contacted with the candidate toxin and the effect on metabolism or morphology is noted in the presence and absence of the candidate. The effect may be cytotoxic—i.e., the cells may themselves exhibit one of the indices of cell death, such as reduced thymidine uptake, slower increase in optical density of the culture, reduced exclusion of vital dyes (e.g., trypan blue), increased release of viability markers such as chromium and rubidium, and the like. The differential response between the toxin-treated cells and the cells absent the toxin is then noted. The strength of the toxin can be assessed by noting the strength of the response.

These assays may be conducted directly as described above or competitively with known toxins. For example, one approach might be to measure the diminution in binding of labeled BT cry toxin in the presence and absence of the toxin candidate.

In addition to simply screening candidates, the screen can be used to devise improved forms of toxins which are more specific or less specific to particular classes of insects as desired. The ability to determine binding affinity ($K_a$ and $K_d$) dissociation and association rates, and cytotoxic effects of a candidate allows quick, accurate and reproducible screening techniques for a large number of toxins and other ligands under identical conditions which was not possible heretofore. Such information will facilitate the selection of the most effective toxins and ligands for any given receptor obtained from any desired host cell.

Competition assays may also employ antibodies that are specifically immunoreactive with the receptor. Such antibodies can be prepared in the conventional manner by administering the purified receptor to a vertebrate animal, monitoring antibody titers and recovering the antisera or the antibody-producing cells for immortalization, to obtain immortalized cells capable of secreting antibodies of the appropriate specificity. Techniques for obtaining immortalized B cells and for screening them for secretion of the desired antibody are now conventional in the art. The resulting monoclonal antibodies may be more effective than the polyclonal antisera as competition reagents; furthermore, the availability of the immortalized cell line secreting the desired antibody assures uniformity of production of the same reagent over time. The information and the structural characteristics of toxins and ligands tested will permit a rational approach to designing more efficient toxins and ligands. Additionally, such assays will lead to a better understanding of the function and the structure/function relationship of both toxin/ligand and $BT-R_1$ analogs. In turn, this will allow the development of highly effective toxins/ ligands. Ligands include natural and modified toxins, antibodies (anti-receptor and antiidiotypic antibodies which mimic a portion of a toxin that binds to a receptor, and whatever small molecules bind the receptors.

Therapeutic Strategies

Advantage may be taken of the ability of receptors to mediate the destruction, dissociation or association of cells, tissues or organs by utilizing the screening assay as a method to identify successful therapeutics in the treatment of, for example, malignancies, metastases and infectious microorganisms which naturally express receptors corresponding to $BT-R_1$. The presence of receptors corresponding to the $BT-R_1$ receptor illustrated herein and members of the family of receptors included in the invention in the undesired cells may be exploited by first assessing the interaction of a proposed therapeutic with the receptors on these cells in culture and then identifying agents which successfully interact with the receptors as useful candidate reagents. Antibodies reactive with these receptors comprise a class of promising therapeutic candidates.

In some applications target cells, tissues, organs, and microorganisms which do not express an effective receptor corresponding to the $BT-R_1$ receptor may be transformed or transfected to express an effective corresponding receptor. These targets then will be killed or manipulated with toxin or other ligands. For instance, yeast cells to be used for toxin assays for a particular insect may be transformed with a genetic construct for expression of the receptor from that insect which corresponds to the $BT-R_1$ receptor.

In another aspect of the invention the receptors corresponding to $BT-R_1$ in certain target cells may be manipulated by modified toxin or other ligands to prevent the normal response to toxin (dissociation, damage and death of membranes, cell, tissues and organisms). For instance, a ligand which binds to a corresponding receptor in such a way that normal receptor function is inhibited would thereby prevent the receptor from initiating the usual destructive effects in the presence of a normal ligand such as a toxin. In other words, the invention enables development of competitive inhibitors of a toxin or other ligand which normally initiates destructive or other effects via a receptor corresponding to $BT-R_1$.

The following examples are intended to illustrate but not to limit the invention.

EXAMPLE 1

Purification and Sequence Determination of $BT-R_1$ Protein

Midguts of *M. sexta* were extracted and the $BT-R_1$ protein purified according to the method of Vadlamudi, R. K. et al. *J Biol Chem* (1993) 268:1233, referenced above and incorporated herein by reference. The electroeluted band was confirmed to contain $BT-R_1$ protein by binding to $^{125}I$-cryIA (b) toxin. In gel electrophoresis, the protein bound to toxin had an apparent weight of approximately 210 kD under reducing and nonreducing conditions.

The purified electroeluted $BT-R_1$ was subjected to cyanogen bromide digestion and the cyanogen bromide fragments separated on a 17% high-resolution tricine SDS-polyacrylamide gel as described by Schagger, H. et al. *Anal Biochem* (1987) 166:368. The separated fragments were transferred to Problott membranes (Applied Biosystems) and five bands were extracted and subjected to microsequencing using standard instrumentation. The amino acid sequences obtained were:

1. (Met) Leu Asp Tyr Glu Val Pro Glu Phe Gln Ser Ile Thr Ile Arg Val Val Ala Thr Asp Asn Asn Asp Thr Arg His Val Gly Val Ala (SEQ ID NO. 3);
2. (Met) X Glu Thr Tyr Glu Leu Ile Ile His Pro Phe Asn Tyr Tyr Ala (SEQ ID NO. 4);
3. (Met) X X X His Gln Leu Pro Leu Ala Gln Asp Ile Lys Asn His (SEQ ID NO. 5);
4. (Met) Phe/Pro Asn/Ile Val Arg/Tyr Val Asp Ile/Gly (SEQ ID NO. 6);
5. (Met) Asn Phe Phe/His Ser Val Asn Arg/Asp Glu (SEQ ID NO. 7).

EXAMPLE 2

Recovery of cDNA

An *M. sexta* cDNA library was constructed from midgut tissue in λgt10 using the Superscript Choice System according to the manufacturer's instructions (Life Technologies, Inc.). Degenerate oligonucleotide probes were constructed based on the peptid sequences determined in Example 1 using the methods and approach described in Zhang, S. et al. *Gene* (1991) 105:61. Synthetic oligonucleotides corresponding to peptides 1–3 of Example 1 were labeled with $\gamma^{32}P$ using polynucleotide kinase and used as probes as described in the standard cloning manual of Maniatis, T. et al. *Molecular Cloning: A Laboratory Manual* (Cold Spring Harbor Laboratory, Cold Spring Harbor, N.Y., 2nd ed. 1989). A clone hybridizing to all three probes identified from 40 positive clones as hybridizing to all three of the probes was plaque-purified from a screen of $4 \times 10^5$ recombinants and subcloned into pBluescript (Stratagene). It contained an insert of 5571 bp.

Double-stranded cDNA in pBluescript was sequenced in both directions by the dideoxy termination method with Sequanase (USB) according to the manufacturer's instructions. The sequencing showed an open reading frame of 4584 base pairs of 1528 amino acids along with a polyadenylation signal at position 5561. The nucleic acid sequence is shown in FIGS. 1A–1M and the deduced amino acid sequence is shown in FIGS. 2A–2H.

Thus, the deduced protein has a molecular mass of 172 kD and a pI of approximately 4.5. The amino acid sequences of the cyanogen bromide fragments of native receptor match perfectly within the deduced amino acid sequence. The open reading frame begins with an ATG that is flanked by the consensus translation initiation sequence GAGATGG for eucaryotic mRNAs as described by Kozak, M. *Nucleic Acids Res* (1987) 15:8125.

As shown in FIGS. 2A–2H, the deduced amino acid sequence includes a putative signal preceding the mature N-terminus Asn-Glu-Arg-etc. Eleven repeats are shown in the extracellular region upstream of the membrane domain at positions 1406–1427.

FIG. 3 compares the BT-R$_1$ sequence obtained herein with other members of the cadherin family. The other cadherins are mouse P cadherin (MP-EC1 ); *Drosophila fat* EC18 (fat EC-18) and protocadherin (PC42-EC-2), and human intestinal transporter.(EC-11) (HPT-1-EC-1). Conserved residues are boxed.

To confirm that the sequenced clone encoded full-length BT-R$_1$ protein, total mRNA was prepared from midguts of *M. sexta* subjected to Northern blot by hybridization with the antisense 4.8 kb SacI fragment of the BT-$R_1$ cDNA clone. The Northern blot analysis was conducted by hybridizing to the antisense probe: at 42° C. and 50% formamide, 5×Denhardt's Reagent, 5×SSCP and 50 μg/ml salmon sperm DNA. The filter was then washed two times with 1×SSC+0.1% SDS and two times with 0.15×SSC+0.1% SDS at 42° C. Each wash was roughly 20 minutes. The filter was then exposed to X-ray film for 24 hours. The 4.8 kb probe hybridized to a single 5.6 kb band.

The BT-$R_1$ clone was translated using rabbit reticulolysate and the resulting translated products were immunoprecipitated with antisera raised against native protein encoded by BT-$R_1$. For the in vitro translation, pBluescript plasmid containing BT-$R_1$ cDNA was linearized and transcribed with $T_3$ polymerase (Pharmacia). The translation was conducted according to manufacturer's instructions with nuclease-treated rabbit reticulolysate (Life Technologies, Inc.). After one hour of incubation 30° C., the reaction mixture was combined with an equal volume of SDS buffer or lysed with 50 mM Tris buffer containing 1% NP40 and 250 mM NaCl (pH 8.0) for immunoprecipitation. Preimmune serum was used as a control. Translation and immunoprecipitation products were electrophoresed on a 7.5% SDS-polyacrylamide gel fixed, treated with Enhance (Dupont NEN), dried and exposed to X-ray film for 12 hours.

Two protein bands of approximately 172 kD and 150 kD as determined by SDS-PAGE were obtained; it is postulated that the 150 kD translation product was due to initiation of translation from an internal methionine at amino acid 242. This is consistent with the observations of Kozak, M. *Mol Cell Biol* (1989) 9:5073.

Thus, both results confirm that a full-length clone was obtained.

EXAMPLE 3

Recombinant Production and Characteristics of the BT-$R_1$ Protein

The BT-$R_1$ cDNA clone was subcloned into the mammalian expression vector pcDNA3 (Invitrogen) and the construct transfected into COS-7 cells. Membranes isolated from tie COS-7 transfectants were solubilized, electrophoresed and ligand blotted with $^{125}$I-cryIA(b) toxin. The cells were harvested 60 hours after transfection, washed with phosphate-buffered saline and lysed by freezing in liquid nitrogen. Cell membranes were prepared by differential centrifugation as described by Elshourbagy, N. A. et al. *J Biol Chem* (1993) 266:3873. Control cells were COS-7 cells transfected with pcDNA3.

The cell membranes (10 μg) were separated on 7.5% SDS-PAGE blotted to a nylon membrane and blocked with Tris-buffered saline containing 5% nonfat dry milk powder, 5% glycerol and 1% Tween-20. The nylon membrane was then incubated with $^{125}$I-cryIA(b) toxin ($2\times10^5$ cpm/ml) for two hours with blocking buffer, dried and exposed to X-ray film at −70° C. The labeled toxin bound to a 210±5 kD protein; the 210 kD band was observed only in lanes containing membranes prepared from either *M. sexta* or COS-7 cells transfected with the. BT-$R_1$ cDNA construct containing 4810 bp of cDNA comprising the open reading frame.

The discrepancy between the 210 kD protein expressed and the calculated 172 kD molecular weight is due to glycosylation of the protein; in vitro translation of the cDNA clone, as described above, which does not result in glycosylation, does produce the 172 kD protein. To verify this, the COS-7 produced protein was subjected to digestion with N-glycosidase-F by first denaturing the purified protein by boiling in 1% SDS for 5 minutes followed by addition of NP-40 to a final concentration of 1% in the presence of 0.1% SDS, and then incubating the denatured protein in sodium phosphate buffer, pH 8.5 at 37° C. with N-glycosidase-F for 10 hours. Controls were incubated under the same conditions without enzyme. Digestion products were separated on a 7.5% SDS-PAGE and stained with Coomassie brilliant blue. This glycosidase treatment reduced the molecular weight of BT-$R_1$ protein from 210 to 190 kD; this indicates N-glycosylation at some of the 16 consensus N-glycosylation sites in the protein. Treatment of BT-$R_1$ with O-glycosidase and neuraminidase did not alter the mobility of the protein.

In addition, embryonic 293 cells were transfected with the BT-$R_1$ cDNA clone in pcDNA3 and incubated with the labeled toxin (0.32 nM) in the presence of increasing concentrations (0 to $10^{-6}$ M) of unlabeled toxin. Nonspecific binding was measured as bound radioactivity in the presence of 1 μM unlabeled toxin. A value for the dissociation constant ($K_d$) of 1015 pM was determined by Scatchard analysis; this is approximately the same value that was obtained for the natural receptor as described by Vadlamudi, R. K. et al. *J Biol Chem* (1993) (supra).

EXAMPLE 4

Physiological Effect of BT Toxin on Modified Embryonic 293 Cells

Both unmodified embryonic 293 cells, and 293 cells which have been modified to produce the BT-$R_1$ receptor as described in Example 3, when cultured in vitro form adherent star-shaped clusters. When BT toxin (200 nM) is added to serum-free medium, the clusters round up and release from the plastic surfaces of the culture dish. This effect is also observed under known conditions of cytotoxicity for 293 cells. The foregoing effect is observed only when the cells are cultured in serum-free medium since the toxin binds to serum and would thus be ineffective under conditions where serum is present.

However, in the presence of anti-receptor antisera, this effect of BT toxin is blocked. Also, when serum is added back to a culture of modified E293 cells which has been treated in serum-free conditions with the toxin, the cells revert to their normal star-shaped adherent cluster shapes. This indicates that the effect of the toxin is reversible.

What is claimed is:

1. A method to assess the binding affinity of a candidate pesticide for an insect receptor that binds *Bacillus thuringiensis* (BT) toxin, which method comprises:
   (a) contacting said candidate pesticide with cells that express BT toxin receptor at their surface and which have been prepared by
      culturing host cells transformed with a recombinant expression system that expresses a BT toxin-binding receptor-encoding polynucleotide, which receptor has the amino acid sequence of the receptor shown in SEQ ID NO: 2, or wherein the receptor is encoded by DNA that hybridizes to the full length cDNA nucleotide sequence of SEQ ID NO: 1 under conditions comprising
      hybridization conditions of 42° C. and 50% formamide, 5×Denhardt's Reagent, 5×SSCP and 50 μg/ml salmon sperm DNA and washing conditions of 1×SSC+0.1% SDS and 0.15×SSC+0.1% SDS at 42° C.
   or an equivalent thereto,
      which expression system comprises, operably linked to said receptor-encoding DNA, an expression control sequence operable in said host cells, and wherein said culturing is performed under conditions that permit production of said receptor, said contacting being under conditions which permit binding of said candidate pesticide to said receptor on said cells; and (b) measuring the binding affinity of said candidate pesticide bound to said cells.

2. A method to assess the cytotoxicity of a candidate pesticide which comprises:

(a) contacting said candidate with cells that express BT toxin receptor at their surface and which have been prepared by culturing host cells transformed with a recombinant expression system that expresses a BT toxin-binding receptor-encoding polynucleotide, which receptor has the amino acid sequence of the receptor shown in SEQ ID NO: 2, or wherein the receptor is encoded by DNA that hybridizes to the full length cDNA nucleotide sequence of SEQ ID NO: 1 under conditions comprising hybridization conditions of 42° C. and 50% formamide, 5×Denhardt's Reagent, 5×SSCP and 50 µg/ml salmon sperm DNA and washing conditions of 1×SSC+0.1% SDS and 0.15×SSC+0.1% SDS at 42° C.

or an equivalent thereto, which expression system comprises, operably linked to said receptor-encoding DNA, an expression control sequence operable in said host cells, and wherein said culturing is performed under conditions that permit production of said receptor, said contacting being under conditions which permit binding of said candidate pesticide to said receptor on said cells; and (b) measuring the cytotoxicity effect of said candidate pesticide on said cells in terms of cell death indices including reduced thymidine uptake, slower increases in optical cell density, reduced exclusion of vital dyes, and increased release of viability markers.

* * * * *

SEQUENCE LISTING

```
<160> NUMBER OF SEQ ID NOS: 11

<210> SEQ ID NO 1
<211> LENGTH: 5582
<212> TYPE: DNA
<213> ORGANISM: M. sexta
<220> FEATURE:
<221> NAME/KEY: CDS
<222> LOCATION: (197)...(5348)

<400> SEQUENCE: 1
gaccaatcgg agtgtggtga atttttggaa aatattttgt gcggttcctt tagttgtgta      60
atatagtact ttagttacaa atttggaata atttggcagc aaaaccatct gcagcaacaa     120
aatcatctgc agctgcgaaa tcatctgcag cagcaaaagc atcttcagga gcgagaaaag     180
ccccaaataa tgtgag atg gca gtt gac gtc cga atc gct gcc ttc ctg ctg    232
                  Met Ala Val Asp Val Arg Ile Ala Ala Phe Leu Leu
                   1               5                  10 gtg ttt ata gcg cct gca gtt tta gct caa gag aga tgt ggg tat atg     280
Val Phe Ile Ala Pro Ala Val Leu Ala Gln Glu Arg Cys Gly Tyr Met
         15                  20                  25 acc gcc atc cca agg cta cca cga ccg gat aat ttg cca gta cta aat     328
Thr Ala Ile Pro Arg Leu Pro Arg Pro Asp Asn Leu Pro Val Leu Asn
     30                  35                  40 ttt gaa ggc cag aca tgg agt cag agg ccc ctg ctc ccc gcc ccg gag     376
Phe Glu Gly Gln Thr Trp Ser Gln Arg Pro Leu Leu Pro Ala Pro Glu
 45                  50                  55                  60 cgg gat gac ctg tgc atg gac gcc tac cac gtg ata aca gcc aac ctc     424
Arg Asp Asp Leu Cys Met Asp Ala Tyr His Val Ile Thr Ala Asn Leu
                 65                  70                  75 ggc acg cag gtc atc tac atg gat gaa gag ata gaa gac gaa atc acc     472
Gly Thr Gln Val Ile Tyr Met Asp Glu Glu Ile Glu Asp Glu Ile Thr
             80                  85                  90
```

```
atc gcc ata ctt aat tat aac gga cca tca act ccg ttc att gaa ctg        520
Ile Ala Ile Leu Asn Tyr Asn Gly Pro Ser Thr Pro Phe Ile Glu Leu
        95                  100                 105 cca ttt tta tcc ggt tcg tac aat ctg ctg atg ccg gtc atc agg aga        568
Pro Phe Leu Ser Gly Ser Tyr Asn Leu Leu Met Pro Val Ile Arg Arg
    110                 115                 120 gtt gac aac ggg gag tgg cat ctc atc atc acg caa aga cag cat tac        616
Val Asp Asn Gly Glu Trp His Leu Ile Ile Thr Gln Arg Gln His Tyr
125                 130                 135                 140 gag ttg ccc ggc atg cag cag tac atg ttc aat gtg cgc gtg gac ggc        664
Glu Leu Pro Gly Met Gln Gln Tyr Met Phe Asn Val Arg Val Asp Gly
                145                 150                 155 cag tcg ctg gtg gca ggc gtg tct ctc gct atc gtc aac ata gat gac        712
Gln Ser Leu Val Ala Gly Val Ser Leu Ala Ile Val Asn Ile Asp Asp
        160                 165                 170 aac gcg ccc atc ata caa aac ttc gag cct tgc cgg gtt cct gaa ctg        760
Asn Ala Pro Ile Ile Gln Asn Phe Glu Pro Cys Arg Val Pro Glu Leu
    175                 180                 185 ggc gag cca ggg ttg aca gaa tgc aca tac caa gta tcg gac gcg gac        808
Gly Glu Pro Gly Leu Thr Glu Cys Thr Tyr Gln Val Ser Asp Ala Asp
190                 195                 200 gga cgg atc agc aca gag ttc atg acg ttc agg atc gac agc gtt cgt        856
Gly Arg Ile Ser Thr Glu Phe Met Thr Phe Arg Ile Asp Ser Val Arg
205                 210                 215                 220 ggc gac gag gag acc ttc tac atc gaa cgg acg aat atc ccc aac caa        904
Gly Asp Glu Glu Thr Phe Tyr Ile Glu Arg Thr Asn Ile Pro Asn Gln
                225                 230                 235 tgg atg tgg cta aat atg acc ata ggc gtt aat acc tcg ctc aac ttc        952
Trp Met Trp Leu Asn Met Thr Ile Gly Val Asn Thr Ser Leu Asn Phe
        240                 245                 250 gtc acc agt ccg ctg cat ata ttc agc gtg aca gcc ctg gac tcg ctc       1000
Val Thr Ser Pro Leu His Ile Phe Ser Val Thr Ala Leu Asp Ser Leu
    255                 260                 265 ccg aac acc cac acg gtg act atg atg gtg caa gtg gcg aat gtg aac       1048
Pro Asn Thr His Thr Val Thr Met Met Val Gln Val Ala Asn Val Asn
270                 275                 280 agc cgt ccg ccg cgc tgg ctg gag atc ttc gct gtc caa cag ttt gaa       1096
Ser Arg Pro Pro Arg Trp Leu Glu Ile Phe Ala Val Gln Gln Phe Glu
285                 290                 295                 300 gag aaa tct tac caa aac ttc aca gtg agg gcg atc gac gga gac act       1144
Glu Lys Ser Tyr Gln Asn Phe Thr Val Arg Ala Ile Asp Gly Asp Thr
                305                 310                 315 gag atc aat atg cct atc aac tac agg ctg atc aca aat gag gaa gac       1192
Glu Ile Asn Met Pro Ile Asn Tyr Arg Leu Ile Thr Asn Glu Glu Asp
        320                 325                 330 aca ttc ttc agc att gag gcc ctg cct ggt gga aaa agc ggg gct gta       1240
Thr Phe Phe Ser Ile Glu Ala Leu Pro Gly Gly Lys Ser Gly Ala Val
    335                 340                 345 ttc ctc gtg tcg cca att gac cgc gac aca ctg caa cga gag gtg ttt       1288
Phe Leu Val Ser Pro Ile Asp Arg Asp Thr Leu Gln Arg Glu Val Phe
350                 355                 360 cca ctt acg atc gtc gct tac aaa tat gat gag gag gcc ttc tcc aca       1336
Pro Leu Thr Ile Val Ala Tyr Lys Tyr Asp Glu Glu Ala Phe Ser Thr
365                 370                 375                 380 tca aca aac gtg gtc atc att gtg aca gac atc aac gac caa aga cct       1384
Ser Thr Asn Val Val Ile Ile Val Thr Asp Ile Asn Asp Gln Arg Pro
                385                 390                 395 gaa cct ata cac aag gaa tat cga ctg gca atc atg gag gag acg ccc       1432
Glu Pro Ile His Lys Glu Tyr Arg Leu Ala Ile Met Glu Glu Thr Pro
        400                 405                 410
```

```
ctg acc ctc aac ttc gat aaa gaa ttc gga ttt cat gat aag gat tta    1480
Leu Thr Leu Asn Phe Asp Lys Glu Phe Gly Phe His Asp Lys Asp Leu
            415                 420                 425 ggt caa aac gct cag tac acg gtg cgt cta gag agc gtg gac cct cca    1528
Gly Gln Asn Ala Gln Tyr Thr Val Arg Leu Glu Ser Val Asp Pro Pro
430                 435                 440 ggc gct gct gag gca ttc tac ata gcg cct gaa gtc ggc tac cag cga    1576
Gly Ala Ala Glu Ala Phe Tyr Ile Ala Pro Glu Val Gly Tyr Gln Arg
445                 450                 455                 460 cag acc ttc atc atg ggc acc ctc aat cac tcc atg ctg gat tac gaa    1624
Gln Thr Phe Ile Met Gly Thr Leu Asn His Ser Met Leu Asp Tyr Glu
            465                 470                 475 gtg cca gag ttt cag agt att acg att cgg gtg gta gcg acc gac aac    1672
Val Pro Glu Phe Gln Ser Ile Thr Ile Arg Val Val Ala Thr Asp Asn
            480                 485                 490 aac gac acg agg cac gtg ggc gtc gcg ttg gtt cac att gac ctc atc    1720
Asn Asp Thr Arg His Val Gly Val Ala Leu Val His Ile Asp Leu Ile
            495                 500                 505 aat tgg aac gat gag cag ccg atc ttc gaa cac gcc gtg cag acc gtc    1768
Asn Trp Asn Asp Glu Gln Pro Ile Phe Glu His Ala Val Gln Thr Val
510                 515                 520 acc ttc gac gag act gaa ggc gag ggg ttc ttc gtc gcc aag gcg gtt    1816
Thr Phe Asp Glu Thr Glu Gly Glu Gly Phe Phe Val Ala Lys Ala Val
525                 530                 535                 540 gca cac gac aga gac atc ggg gat gtc gtc gag cat act tta ttg ggt    1864
Ala His Asp Arg Asp Ile Gly Asp Val Val Glu His Thr Leu Leu Gly
            545                 550                 555 aac gct gtt aac ttc ctg acc atc gac aaa ctc acc ggc gac atc cgc    1912
Asn Ala Val Asn Phe Leu Thr Ile Asp Lys Leu Thr Gly Asp Ile Arg
            560                 565                 570 gtc tca gct aac gac tcc ttc aac tac cat cga gaa agt gaa tta ttt    1960
Val Ser Ala Asn Asp Ser Phe Asn Tyr His Arg Glu Ser Glu Leu Phe
575                 580                 585 gtg cag gtg cga gct aca gac acg ctg ggc gaa ccc ttc cac acg gcg    2008
Val Gln Val Arg Ala Thr Asp Thr Leu Gly Glu Pro Phe His Thr Ala
590                 595                 600 acg tca cag ctg gtc ata cga cta aat gac atc aac aac acg cca ccc    2056
Thr Ser Gln Leu Val Ile Arg Leu Asn Asp Ile Asn Asn Thr Pro Pro
605                 610                 615                 620 acc tta cgg ctg cct cga ggc agt ccc caa gtg gag gag aac gtg cct    2104
Thr Leu Arg Leu Pro Arg Gly Ser Pro Gln Val Glu Glu Asn Val Pro
            625                 630                 635 gat ggc cac gtc atc acc cag gag tta cgc gcc acc gac ccc gac acc    2152
Asp Gly His Val Ile Thr Gln Glu Leu Arg Ala Thr Asp Pro Asp Thr
            640                 645                 650 acg gcc gat ctg cgc ttc gag ata aac tgg gac acc tct ttc gcc acc    2200
Thr Ala Asp Leu Arg Phe Glu Ile Asn Trp Asp Thr Ser Phe Ala Thr
            655                 660                 665 aag caa ggc cgc cag gct aac ccc gac gag ttt agg aat tgc gtg gaa    2248
Lys Gln Gly Arg Gln Ala Asn Pro Asp Glu Phe Arg Asn Cys Val Glu
670                 675                 680 atc gag acc atc ttc ccc gag att aac aac cgg gga ctg gct atc ggc    2296
Ile Glu Thr Ile Phe Pro Glu Ile Asn Asn Arg Gly Leu Ala Ile Gly
685                 690                 695                 700 cgc gtt gta gcg cgc gaa atc aga cac aac gtg acc ata gac tac gag    2344
Arg Val Val Ala Arg Glu Ile Arg His Asn Val Thr Ile Asp Tyr Glu
            705                 710                 715 gag ttt gag gtc ctc tcc ctc aca gtg agg gtg cgt gac ctt aac acc    2392
Glu Phe Glu Val Leu Ser Leu Thr Val Arg Val Arg Asp Leu Asn Thr
            720                 725                 730
```

```
gtc tac gga gac gac tac gac gaa tcg atg ctc aca ata act ata atc        2440
Val Tyr Gly Asp Asp Tyr Asp Glu Ser Met Leu Thr Ile Thr Ile Ile
        735                 740                 745 gat atg aac gac aac gcg ccg gtg tgg gtg gag ggg act ctg gag cag        2488
Asp Met Asn Asp Asn Ala Pro Val Trp Val Glu Gly Thr Leu Glu Gln
750                 755                 760 aac ttc cga gtc cgc gag atg tcg gcg ggc ggg ctc gtg gtg ggc tcc        2536
Asn Phe Arg Val Arg Glu Met Ser Ala Gly Gly Leu Val Val Gly Ser
765                 770                 775                 780 gtg cgc gcg gac gac atc gac gga ccg ctc tac aac caa gtg cga tac        2584
Val Arg Ala Asp Asp Ile Asp Gly Pro Leu Tyr Asn Gln Val Arg Tyr
                785                 790                 795 acc att ttc cct cgt gaa gac aca gat aag gac ctg ata atg atc gac        2632
Thr Ile Phe Pro Arg Glu Asp Thr Asp Lys Asp Leu Ile Met Ile Asp
            800                 805                 810 ttc ctc acg ggt caa att tcc gtg aac aca agc ggc gcc atc gac gcg        2680
Phe Leu Thr Gly Gln Ile Ser Val Asn Thr Ser Gly Ala Ile Asp Ala
        815                 820                 825 gat act cct cca cgc ttc cac ctc tac tat aca gtg gtc gct agt gac        2728
Asp Thr Pro Pro Arg Phe His Leu Tyr Tyr Thr Val Val Ala Ser Asp
    830                 835                 840 cga tgc tcg aca gaa gat cct gca gat tgc ccc cct gac ccg act tat        2776
Arg Cys Ser Thr Glu Asp Pro Ala Asp Cys Pro Pro Asp Pro Thr Tyr
845                 850                 855                 860 tgg gaa acc gaa gga aat atc aca atc cac atc acc gac acg aac aac        2824
Trp Glu Thr Glu Gly Asn Ile Thr Ile His Ile Thr Asp Thr Asn Asn
                865                 870                 875 aag gtc ccg cag gcg gaa acg act aag ttc gat acc gtc gtg tat att        2872
Lys Val Pro Gln Ala Glu Thr Thr Lys Phe Asp Thr Val Val Tyr Ile
            880                 885                 890 tac gag aac gca acc cac tta gac gag gtg gtc act ctg ata gcc agt        2920
Tyr Glu Asn Ala Thr His Leu Asp Glu Val Val Thr Leu Ile Ala Ser
        895                 900                 905 gat ctt gac aga gac gaa ata tac cac acg gtg agc tac gtc atc aat        2968
Asp Leu Asp Arg Asp Glu Ile Tyr His Thr Val Ser Tyr Val Ile Asn
    910                 915                 920 tat gca gtg aac cct cga ctg atg aac ttc ttc tcc gtg aac cga gag        3016
Tyr Ala Val Asn Pro Arg Leu Met Asn Phe Phe Ser Val Asn Arg Glu
925                 930                 935                 940 acc ggc ctg gtg tac gtg gac tat gag acc cag ggt agt ggc gag gtg        3064
Thr Gly Leu Val Tyr Val Asp Tyr Glu Thr Gln Gly Ser Gly Glu Val
                945                 950                 955 ctg gac cgt gat ggt gat gaa cca acg cac cgt atc ttc ttc aac ctc        3112
Leu Asp Arg Asp Gly Asp Glu Pro Thr His Arg Ile Phe Phe Asn Leu
            960                 965                 970 atc gac aac ttc atg ggg gaa gga gaa ggt aac aga aat cag aac gac        3160
Ile Asp Asn Phe Met Gly Glu Gly Glu Gly Asn Arg Asn Gln Asn Asp
        975                 980                 985 aca gaa gtt ctc gtt atc ttg ttg gat gtg aat gac aat gct cct gaa        3208
Thr Glu Val Leu Val Ile Leu Leu Asp Val Asn Asp Asn Ala Pro Glu
    990                 995                 1000 ttg cca ccg ccg agc gaa ctc tct tgg act ata tct gag aac ctt aag        3256
Leu Pro Pro Pro Ser Glu Leu Ser Trp Thr Ile Ser Glu Asn Leu Lys
1005                1010                1015                1020 cag ggc gtc cgt ctt gaa cca cat atc ttc gcc ccg gac cgc gac gag        3304
Gln Gly Val Arg Leu Glu Pro His Ile Phe Ala Pro Asp Arg Asp Glu
                1025                1030                1035 ccc gac aca gac aac tcc agg gtc ggc tac gag atc ctg aac ctc agc        3352
Pro Asp Thr Asp Asn Ser Arg Val Gly Tyr Glu Ile Leu Asn Leu Ser
            1040                1045                1050
```

-continued

| | |
|---|---|
| acg gag cgg gac atc gaa gtg ccg gag ctg ttt gtg atg ata cag atc<br>Thr Glu Arg Asp Ile Glu Val Pro Glu Leu Phe Val Met Ile Gln Ile<br>    1055                    1060                    1065 | 3400 |
| gcg aac gtc acg gga gag ctg gag acc gcc atg gac ctc aag gga tat<br>Ala Asn Val Thr Gly Glu Leu Glu Thr Ala Met Asp Leu Lys Gly Tyr<br>1070                    1075                    1080 | 3448 |
| tgg ggg acg tac gct ata cat ata cgg gca ttc gac cac ggc att ccg<br>Trp Gly Thr Tyr Ala Ile His Ile Arg Ala Phe Asp His Gly Ile Pro<br>1085                    1090                    1095                    1100 | 3496 |
| caa atg tcc atg aac gag aca tat gag ctg atc atc cat ccg ttc aac<br>Gln Met Ser Met Asn Glu Thr Tyr Glu Leu Ile Ile His Pro Phe Asn<br>    1105                    1110                    1115 | 3544 |
| tac tac gcg cct gag ttc gtc ttc ccg acc aac gat gcc gtc ata cga<br>Tyr Tyr Ala Pro Glu Phe Val Phe Pro Thr Asn Asp Ala Val Ile Arg<br>            1120                    1125                    1130 | 3592 |
| ctt gcg agg gaa cga gct gta atc aat gga gtt cta gcg aca gtg aac<br>Leu Ala Arg Glu Arg Ala Val Ile Asn Gly Val Leu Ala Thr Val Asn<br>                1135                    1140                    1145 | 3640 |
| gga gag ttc ttg gag cgg ata tcg gcg act gat ccg gac gga ctc cac<br>Gly Glu Phe Leu Glu Arg Ile Ser Ala Thr Asp Pro Asp Gly Leu His<br>            1150                    1155                    1160 | 3688 |
| gcg ggc gtc gtc acc ttc caa gtg gta ggc gat gag gaa tca caa cgg<br>Ala Gly Val Val Thr Phe Gln Val Val Gly Asp Glu Glu Ser Gln Arg<br>1165                    1170                    1175                    1180 | 3736 |
| tac ttt caa gta gtt aac gat ggc gag aac ctc ggc tcg ttg agg tta<br>Tyr Phe Gln Val Val Asn Asp Gly Glu Asn Leu Gly Ser Leu Arg Leu<br>                1185                    1190                    1195 | 3784 |
| ctg caa gcc gtt cca gag gag atc agg gag ttc cgg ata acg att cgc<br>Leu Gln Ala Val Pro Glu Glu Ile Arg Glu Phe Arg Ile Thr Ile Arg<br>            1200                    1205                    1210 | 3832 |
| gct aca gac cag gga acg gac cca gga ccg ctg tcc acg gac atg acg<br>Ala Thr Asp Gln Gly Thr Asp Pro Gly Pro Leu Ser Thr Asp Met Thr<br>                1215                    1220                    1225 | 3880 |
| ttc aga gtt gtt ttt gtg ccc acg caa gga gaa cct aga ttc gcg tcc<br>Phe Arg Val Val Phe Val Pro Thr Gln Gly Glu Pro Arg Phe Ala Ser<br>    1230                    1235                    1240 | 3928 |
| tca gaa cat gct gtc gct ttc ata gaa aag agt gcc ggc atg gaa gag<br>Ser Glu His Ala Val Ala Phe Ile Glu Lys Ser Ala Gly Met Glu Glu<br>1245                    1250                    1255                    1260 | 3976 |
| tct cac caa ctt cct cta gca caa gac atc aag aac cat ctc tgt gaa<br>Ser His Gln Leu Pro Leu Ala Gln Asp Ile Lys Asn His Leu Cys Glu<br>            1265                    1270                    1275 | 4024 |
| gac gac tgt cac agc att tac tat cgt att atc gat ggc aac agc gaa<br>Asp Asp Cys His Ser Ile Tyr Tyr Arg Ile Ile Asp Gly Asn Ser Glu<br>                1280                    1285                    1290 | 4072 |
| ggt cat ttc ggc ctg gat cct gtt cgc aac agg ttg ttc ctg aag aaa<br>Gly His Phe Gly Leu Asp Pro Val Arg Asn Arg Leu Phe Leu Lys Lys<br>            1295                    1300                    1305 | 4120 |
| gag ctg ata agg gaa caa agt gcc tcc cac act ctg caa gtg gcg gct<br>Glu Leu Ile Arg Glu Gln Ser Ala Ser His Thr Leu Gln Val Ala Ala<br>    1310                    1315                    1320 | 4168 |
| agt aac tcg ccc gat ggt ggc att cca ctt cct gct tcc atc ctt act<br>Ser Asn Ser Pro Asp Gly Gly Ile Pro Leu Pro Ala Ser Ile Leu Thr<br>1325                    1330                    1335                    1340 | 4216 |
| gtc act gtt acc gtg agg gag gca gac cct cgt cca gtg ttt gtg agg<br>Val Thr Val Thr Val Arg Glu Ala Asp Pro Arg Pro Val Phe Val Arg<br>            1345                    1350                    1355 | 4264 |
| gaa ttg tac acc gca ggg ata tcc aca gcg gac tcc atc ggc aga gag<br>Glu Leu Tyr Thr Ala Gly Ile Ser Thr Ala Asp Ser Ile Gly Arg Glu<br>                1360                    1365                    1370 | 4312 |

-continued

| | |
|---|---|
| ctg ctc aga tta cat gcg acc cag tct gaa ggc tcg gcc att act tat<br>Leu Leu Arg Leu His Ala Thr Gln Ser Glu Gly Ser Ala Ile Thr Tyr<br>　　1375　　　　　　　　1380　　　　　　　　1385 | 4360 |
| gct ata gac tac gat aca atg gta gtg gac ccc agc ctg gag gca gtg<br>Ala Ile Asp Tyr Asp Thr Met Val Val Asp Pro Ser Leu Glu Ala Val<br>1390　　　　　　　　1395　　　　　　　　1400 | 4408 |
| aga cag tcg gct ttc gta ctg aac gct caa acc gga gtg ctg acg ctt<br>Arg Gln Ser Ala Phe Val Leu Asn Ala Gln Thr Gly Val Leu Thr Leu<br>1405　　　　　　　　1410　　　　　　　　1415　　　　　　　　1420 | 4456 |
| aat atc cag ccc acg gcc acg atg cat gga ctg ttc aaa ttc gaa gtc<br>Asn Ile Gln Pro Thr Ala Thr Met His Gly Leu Phe Lys Phe Glu Val<br>　　　　　　　1425　　　　　　　　1430　　　　　　　　1435 | 4504 |
| aca gct act gac acg gcc ggc gct cag gac cgc acc gac gtc acc gtg<br>Thr Ala Thr Asp Thr Ala Gly Ala Gln Asp Arg Thr Asp Val Thr Val<br>　　　　　　　1440　　　　　　　　1445　　　　　　　　1450 | 4552 |
| tac gtg gta tcc tcg cag aac cgc gtc tac ttc gtg ttc gtc aac acg<br>Tyr Val Val Ser Ser Gln Asn Arg Val Tyr Phe Val Phe Val Asn Thr<br>　　　　　　　1455　　　　　　　　1460　　　　　　　　1465 | 4600 |
| ctg caa cag gtc gaa gac aac aga gac ttt atc gcg gac acc ttc agc<br>Leu Gln Gln Val Glu Asp Asn Arg Asp Phe Ile Ala Asp Thr Phe Ser<br>　　　　　　　1470　　　　　　　　1475　　　　　　　　1480 | 4648 |
| gct ggg ttc aac atg acc tgc aac atc gac caa gtg gtg ccc gct aac<br>Ala Gly Phe Asn Met Thr Cys Asn Ile Asp Gln Val Val Pro Ala Asn<br>1485　　　　　　　　1490　　　　　　　　1495　　　　　　　　1500 | 4696 |
| gac ccc gtc acc ggc gtg gcg ctg gag cac agc acg cag atg cgc ggc<br>Asp Pro Val Thr Gly Val Ala Leu Glu His Ser Thr Gln Met Arg Gly<br>　　　　　　　1505　　　　　　　　1510　　　　　　　　1515 | 4744 |
| cac ttc ata cgg gac aac gta ccc gta ctc gct gat gag ata gaa cag<br>His Phe Ile Arg Asp Asn Val Pro Val Leu Ala Asp Glu Ile Glu Gln<br>　　　　　　　1520　　　　　　　　1525　　　　　　　　1530 | 4792 |
| atc cgt agt gac cta gtc ctc ctg agc tcg ata caa aca acg ctg gcg<br>Ile Arg Ser Asp Leu Val Leu Leu Ser Ser Ile Gln Thr Thr Leu Ala<br>　　　　　　　1535　　　　　　　　1540　　　　　　　　1545 | 4840 |
| gcg cga tcg ctg gtg ttg cag gac ttg ttg acc aac tcc agc ccg gac<br>Ala Arg Ser Leu Val Leu Gln Asp Leu Leu Thr Asn Ser Ser Pro Asp<br>1550　　　　　　　　1555　　　　　　　　1560 | 4888 |
| tcg gcg cct gac tcg agc ctc acg gtg tac gtg ctg gcc tca ctg tct<br>Ser Ala Pro Asp Ser Ser Leu Thr Val Tyr Val Leu Ala Ser Leu Ser<br>1565　　　　　　　　1570　　　　　　　　1575　　　　　　　　1580 | 4936 |
| gct gtg ctc ggt ttc atg tgc ctt gtg cta ctg ctt acc ttc atc atc<br>Ala Val Leu Gly Phe Met Cys Leu Val Leu Leu Leu Thr Phe Ile Ile<br>　　　　　　　1585　　　　　　　　1590　　　　　　　　1595 | 4984 |
| agg act aga gcg cta aac cga cgg ttg gaa gcc ctg tcg atg acg aag<br>Arg Thr Arg Ala Leu Asn Arg Arg Leu Glu Ala Leu Ser Met Thr Lys<br>　　　　　　　1600　　　　　　　　1605　　　　　　　　1610 | 5032 |
| tac ggc tca ctg gac tct gga ttg aac cgc gcc ggc atc gcc gcc ccc<br>Tyr Gly Ser Leu Asp Ser Gly Leu Asn Arg Ala Gly Ile Ala Ala Pro<br>　　　　　　　1615　　　　　　　　1620　　　　　　　　1625 | 5080 |
| ggc acc aac aaa cac act gtg gaa ggc tcc aac cct atc ttc aat gaa<br>Gly Thr Asn Lys His Thr Val Glu Gly Ser Asn Pro Ile Phe Asn Glu<br>　　　　　　　1630　　　　　　　　1635　　　　　　　　1640 | 5128 |
| gca ata aag acg cca gat tta gat gcc att agc gag ggt tcc aac gac<br>Ala Ile Lys Thr Pro Asp Leu Asp Ala Ile Ser Glu Gly Ser Asn Asp<br>1645　　　　　　　　1650　　　　　　　　1655　　　　　　　　1660 | 5176 |
| tct gat ctg atc ggc atc gaa gat ctt ccg cac ttt ggc aac gtc ttc<br>Ser Asp Leu Ile Gly Ile Glu Asp Leu Pro His Phe Gly Asn Val Phe<br>　　　　　　　1665　　　　　　　　1670　　　　　　　　1675 | 5224 |
| atg gat cct gag gtg aac gaa aag gca aat ggt tat ccc gaa gtc gca<br>Met Asp Pro Glu Val Asn Glu Lys Ala Asn Gly Tyr Pro Glu Val Ala<br>　　　　　　　1680　　　　　　　　1685　　　　　　　　1690 | 5272 |

-continued

```
aac cac aac aac aac ttc gct ttc aac ccg act ccc ttc tcg cct gag    5320
Asn His Asn Asn Asn Phe Ala Phe Asn Pro Thr Pro Phe Ser Pro Glu
        1695                1700                1705 ttc gtt aac gga cag ttc aga aag atc t agaagataac aacactagtt        5368
Phe Val Asn Gly Gln Phe Arg Lys Ile
    1710                1715 aagatcatta attttggagt ttggaattaa gattttgaa aggatagttg tgataagcct   5428 gtgatttta aaactgtaat tgaaaaaaaa aattgagacc tccatttaag ctcttgctct   5488
catctcatca aattttataa aatgccatta gtcattaaga tactcgattt aatttaagat  5548
tatttaagat attatgtaaa ataaatatat tgtc                              5582

<210> SEQ ID NO 2
<211> LENGTH: 1717
<212> TYPE: PRT
<213> ORGANISM: M. sexta

<400> SEQUENCE: 2

Met Ala Val Asp Val Arg Ile Ala Ala Phe Leu Leu Val Phe Ile Ala
 1               5                  10                  15

Pro Ala Val Leu Ala Gln Glu Arg Cys Gly Tyr Met Thr Ala Ile Pro
            20                  25                  30

Arg Leu Pro Arg Pro Asp Asn Leu Pro Val Leu Asn Phe Glu Gly Gln
        35                  40                  45

Thr Trp Ser Gln Arg Pro Leu Leu Pro Ala Pro Glu Arg Asp Asp Leu
    50                  55                  60

Cys Met Asp Ala Tyr His Val Ile Thr Ala Asn Leu Gly Thr Gln Val
65                  70                  75                  80

Ile Tyr Met Asp Glu Glu Ile Glu Asp Glu Ile Thr Ile Ala Ile Leu
                85                  90                  95

Asn Tyr Asn Gly Pro Ser Thr Pro Phe Ile Glu Leu Pro Phe Leu Ser
            100                 105                 110

Gly Ser Tyr Asn Leu Leu Met Pro Val Ile Arg Arg Val Asp Asn Gly
        115                 120                 125

Glu Trp His Leu Ile Ile Thr Gln Arg Gln His Tyr Glu Leu Pro Gly
    130                 135                 140

Met Gln Gln Tyr Met Phe Asn Val Arg Val Asp Gly Gln Ser Leu Val
145                 150                 155                 160

Ala Gly Val Ser Leu Ala Ile Val Asn Ile Asp Asp Asn Ala Pro Ile
                165                 170                 175

Ile Gln Asn Phe Glu Pro Cys Arg Val Pro Glu Leu Gly Glu Pro Gly
            180                 185                 190

Leu Thr Glu Cys Thr Tyr Gln Val Ser Asp Ala Asp Gly Arg Ile Ser
        195                 200                 205

Thr Glu Phe Met Thr Phe Arg Ile Asp Ser Val Arg Gly Asp Glu Glu
    210                 215                 220

Thr Phe Tyr Ile Glu Arg Thr Asn Ile Pro Asn Gln Trp Met Trp Leu
225                 230                 235                 240

Asn Met Thr Ile Gly Val Asn Thr Ser Leu Asn Phe Val Thr Ser Pro
                245                 250                 255

Leu His Ile Phe Ser Val Thr Ala Leu Asp Ser Leu Pro Asn Thr His
            260                 265                 270

Thr Val Thr Met Met Val Gln Val Ala Asn Val Asn Ser Arg Pro Pro
        275                 280                 285
```

-continued

```
Arg Trp Leu Glu Ile Phe Ala Val Gln Gln Phe Glu Lys Ser Tyr
    290             295             300
Gln Asn Phe Thr Val Arg Ala Ile Asp Gly Asp Thr Glu Ile Asn Met
305                 310             315                 320
Pro Ile Asn Tyr Arg Leu Ile Thr Asn Glu Glu Asp Thr Phe Phe Ser
                325             330             335
Ile Glu Ala Leu Pro Gly Gly Lys Ser Gly Ala Val Phe Leu Val Ser
            340             345             350
Pro Ile Asp Arg Asp Thr Leu Gln Arg Glu Val Phe Pro Leu Thr Ile
            355             360             365
Val Ala Tyr Lys Tyr Asp Glu Glu Ala Phe Ser Thr Ser Thr Asn Val
    370             375             380
Val Ile Ile Val Thr Asp Ile Asn Asp Gln Arg Pro Glu Pro Ile His
385                 390             395                 400
Lys Glu Tyr Arg Leu Ala Ile Met Glu Glu Thr Pro Leu Thr Leu Asn
                405             410             415
Phe Asp Lys Glu Phe Gly Phe His Asp Lys Asp Leu Gly Gln Asn Ala
            420             425             430
Gln Tyr Thr Val Arg Leu Glu Ser Val Asp Pro Pro Gly Ala Ala Glu
            435             440             445
Ala Phe Tyr Ile Ala Pro Glu Val Gly Tyr Gln Arg Gln Thr Phe Ile
    450             455             460
Met Gly Thr Leu Asn His Ser Met Leu Asp Tyr Glu Val Pro Glu Phe
465                 470             475                 480
Gln Ser Ile Thr Ile Arg Val Val Ala Thr Asp Asn Asn Asp Thr Arg
                485             490             495
His Val Gly Val Ala Leu Val His Ile Asp Leu Ile Asn Trp Asn Asp
            500             505             510
Glu Gln Pro Ile Phe Glu His Ala Val Gln Thr Val Thr Phe Asp Glu
            515             520             525
Thr Glu Gly Glu Gly Phe Phe Val Ala Lys Ala Val Ala His Asp Arg
    530             535             540
Asp Ile Gly Asp Val Val Glu His Thr Leu Leu Gly Asn Ala Val Asn
545                 550             555                 560
Phe Leu Thr Ile Asp Lys Leu Thr Gly Asp Ile Arg Val Ser Ala Asn
                565             570             575
Asp Ser Phe Asn Tyr His Arg Glu Ser Glu Leu Phe Val Gln Val Arg
            580             585             590
Ala Thr Asp Thr Leu Gly Glu Pro Phe His Thr Ala Thr Ser Gln Leu
            595             600             605
Val Ile Arg Leu Asn Asp Ile Asn Asn Thr Pro Pro Thr Leu Arg Leu
    610             615             620
Pro Arg Gly Ser Pro Gln Val Glu Glu Asn Val Pro Asp Gly His Val
625                 630             635                 640
Ile Thr Gln Glu Leu Arg Ala Thr Asp Pro Asp Thr Ala Asp Leu
                645             650             655
Arg Phe Glu Ile Asn Trp Asp Thr Ser Phe Ala Thr Lys Gln Gly Arg
                660             665             670
Gln Ala Asn Pro Asp Glu Phe Arg Asn Cys Val Glu Ile Glu Thr Ile
            675             680             685
Phe Pro Glu Ile Asn Asn Arg Gly Leu Ala Ile Gly Arg Val Val Ala
690                 695             700
```

-continued

```
Arg Glu Ile Arg His Asn Val Thr Ile Asp Tyr Glu Phe Glu Val
705                 710                 715                 720

Leu Ser Leu Thr Val Arg Val Arg Asp Leu Asn Thr Val Tyr Gly Asp
            725                 730                 735

Asp Tyr Asp Glu Ser Met Leu Thr Ile Thr Ile Asp Met Asn Asp
            740                 745                 750

Asn Ala Pro Val Trp Val Glu Gly Thr Leu Gln Asn Phe Arg Val
            755                 760                 765

Arg Glu Met Ser Ala Gly Gly Leu Val Val Gly Ser Val Arg Ala Asp
770                 775                 780

Asp Ile Asp Gly Pro Leu Tyr Asn Gln Val Arg Tyr Thr Ile Phe Pro
785                 790                 795                 800

Arg Glu Asp Thr Asp Lys Asp Leu Ile Met Ile Asp Phe Leu Thr Gly
                805                 810                 815

Gln Ile Ser Val Asn Thr Ser Gly Ala Ile Asp Ala Asp Thr Pro Pro
            820                 825                 830

Arg Phe His Leu Tyr Tyr Thr Val Val Ala Ser Asp Arg Cys Ser Thr
            835                 840                 845

Glu Asp Pro Ala Asp Cys Pro Pro Asp Pro Thr Tyr Trp Glu Thr Glu
850                 855                 860

Gly Asn Ile Thr Ile His Ile Thr Asp Thr Asn Asn Lys Val Pro Gln
865                 870                 875                 880

Ala Glu Thr Thr Lys Phe Asp Thr Val Val Tyr Ile Tyr Glu Asn Ala
                885                 890                 895

Thr His Leu Asp Glu Val Val Thr Leu Ile Ala Ser Asp Leu Asp Arg
            900                 905                 910

Asp Glu Ile Tyr His Thr Val Ser Tyr Val Ile Asn Tyr Ala Val Asn
            915                 920                 925

Pro Arg Leu Met Asn Phe Phe Ser Val Asn Arg Glu Thr Gly Leu Val
            930                 935                 940

Tyr Val Asp Tyr Glu Thr Gln Gly Ser Gly Glu Val Leu Asp Arg Asp
945                 950                 955                 960

Gly Asp Glu Pro Thr His Arg Ile Phe Phe Asn Leu Ile Asp Asn Phe
                965                 970                 975

Met Gly Glu Gly Glu Gly Asn Arg Asn Gln Asn Asp Thr Glu Val Leu
            980                 985                 990

Val Ile Leu Leu Asp Val Asn Asp Asn Ala Pro Glu Leu Pro Pro Pro
            995                 1000                1005

Ser Glu Leu Ser Trp Thr Ile Ser Glu Asn Leu Lys Gln Gly Val Arg
            1010                1015                1020

Leu Glu Pro His Ile Phe Ala Pro Asp Arg Asp Glu Pro Asp Thr Asp
1025                1030                1035                1040

Asn Ser Arg Val Gly Tyr Glu Ile Leu Asn Leu Ser Thr Glu Arg Asp
            1045                1050                1055

Ile Glu Val Pro Glu Leu Phe Val Met Ile Gln Ile Ala Asn Val Thr
            1060                1065                1070

Gly Glu Leu Glu Thr Ala Met Asp Leu Lys Gly Tyr Trp Gly Thr Tyr
            1075                1080                1085

Ala Ile His Ile Arg Ala Phe Asp His Gly Ile Pro Gln Met Ser Met
            1090                1095                1100

Asn Glu Thr Tyr Glu Leu Ile Ile His Pro Phe Asn Tyr Tyr Ala Pro
1105                1110                1115                1120
```

-continued

Glu Phe Val Phe Pro Thr Asn Asp Ala Val Ile Arg Leu Ala Arg Glu
            1125                1130                1135

Arg Ala Val Ile Asn Gly Val Leu Ala Thr Val Asn Gly Glu Phe Leu
        1140                1145                1150

Glu Arg Ile Ser Ala Thr Asp Pro Asp Gly Leu His Ala Gly Val Val
            1155                1160                1165

Thr Phe Gln Val Val Gly Asp Glu Glu Ser Gln Arg Tyr Phe Gln Val
        1170                1175                1180

Val Asn Asp Gly Glu Asn Leu Gly Ser Leu Arg Leu Leu Gln Ala Val
1185                1190                1195                1200

Pro Glu Glu Ile Arg Glu Phe Arg Ile Thr Ile Arg Ala Thr Asp Gln
            1205                1210                1215

Gly Thr Asp Pro Gly Pro Leu Ser Thr Asp Met Thr Phe Arg Val Val
            1220                1225                1230

Phe Val Pro Thr Gln Gly Glu Pro Arg Phe Ala Ser Ser Glu His Ala
            1235                1240                1245

Val Ala Phe Ile Glu Lys Ser Ala Gly Met Glu Glu Ser His Gln Leu
        1250                1255                1260

Pro Leu Ala Gln Asp Ile Lys Asn His Leu Cys Glu Asp Asp Cys His
1265                1270                1275                1280

Ser Ile Tyr Tyr Arg Ile Ile Asp Gly Asn Ser Glu Gly His Phe Gly
            1285                1290                1295

Leu Asp Pro Val Arg Asn Arg Leu Phe Leu Lys Lys Glu Leu Ile Arg
            1300                1305                1310

Glu Gln Ser Ala Ser His Thr Leu Gln Val Ala Ala Ser Asn Ser Pro
            1315                1320                1325

Asp Gly Gly Ile Pro Leu Pro Ala Ser Ile Leu Thr Val Thr Val Thr
        1330                1335                1340

Val Arg Glu Ala Asp Pro Arg Pro Val Phe Val Arg Glu Leu Tyr Thr
1345                1350                1355                1360

Ala Gly Ile Ser Thr Ala Asp Ser Ile Gly Arg Glu Leu Leu Arg Leu
            1365                1370                1375

His Ala Thr Gln Ser Glu Gly Ser Ala Ile Thr Tyr Ala Ile Asp Tyr
            1380                1385                1390

Asp Thr Met Val Val Asp Pro Ser Leu Glu Ala Val Arg Gln Ser Ala
        1395                1400                1405

Phe Val Leu Asn Ala Gln Thr Gly Val Leu Thr Leu Asn Ile Gln Pro
    1410                1415                1420

Thr Ala Thr Met His Gly Leu Phe Lys Phe Glu Val Thr Ala Thr Asp
1425                1430                1435                1440

Thr Ala Gly Ala Gln Asp Arg Thr Asp Val Thr Val Tyr Val Val Ser
            1445                1450                1455

Ser Gln Asn Arg Val Tyr Phe Val Phe Val Asn Thr Leu Gln Gln Val
            1460                1465                1470

Glu Asp Asn Arg Asp Phe Ile Ala Asp Thr Phe Ser Ala Gly Phe Asn
        1475                1480                1485

Met Thr Cys Asn Ile Asp Gln Val Val Pro Ala Asn Asp Pro Val Thr
        1490                1495                1500

Gly Val Ala Leu Glu His Ser Thr Gln Met Arg Gly His Phe Ile Arg
1505                1510                1515                1520

Asp Asn Val Pro Val Leu Ala Asp Glu Ile Glu Gln Ile Arg Ser Asp
            1525                1530                1535

-continued

```
Leu Val Leu Leu Ser Ser Ile Gln Thr Thr Leu Ala Ala Arg Ser Leu
            1540                1545                1550

Val Leu Gln Asp Leu Leu Thr Asn Ser Ser Pro Asp Ser Ala Pro Asp
        1555                1560                1565

Ser Ser Leu Thr Val Tyr Val Leu Ala Ser Leu Ser Ala Val Leu Gly
    1570                1575                1580

Phe Met Cys Leu Val Leu Leu Leu Thr Phe Ile Ile Arg Thr Arg Ala
1585                1590                1595                1600

Leu Asn Arg Arg Leu Glu Ala Leu Ser Met Thr Lys Tyr Gly Ser Leu
            1605                1610                1615

Asp Ser Gly Leu Asn Arg Ala Gly Ile Ala Ala Pro Gly Thr Asn Lys
        1620                1625                1630

His Thr Val Glu Gly Ser Asn Pro Ile Phe Asn Glu Ala Ile Lys Thr
    1635                1640                1645

Pro Asp Leu Asp Ala Ile Ser Glu Gly Ser Asn Asp Ser Asp Leu Ile
1650                1655                1660

Gly Ile Glu Asp Leu Pro His Phe Gly Asn Val Phe Met Asp Pro Glu
1665                1670                1675                1680

Val Asn Glu Lys Ala Asn Gly Tyr Pro Glu Val Ala Asn His Asn Asn
            1685                1690                1695

Asn Phe Ala Phe Asn Pro Thr Pro Phe Ser Pro Glu Phe Val Asn Gly
        1700                1705                1710

Gln Phe Arg Lys Ile
        1715

<210> SEQ ID NO 3
<211> LENGTH: 30
<212> TYPE: PRT
<213> ORGANISM: M. sexta

<400> SEQUENCE: 3

Met Leu Asp Tyr Glu Val Pro Glu Phe Gln Ser Ile Thr Ile Arg Val
1               5                   10                  15

Val Ala Thr Asp Asn Asn Asp Thr Arg His Val Gly Val Ala
            20                  25                  30

<210> SEQ ID NO 4
<211> LENGTH: 16
<212> TYPE: PRT
<213> ORGANISM: M. sexta
<220> FEATURE:
<221> NAME/KEY: VARIANT
<222> LOCATION: (1)...(16)
<223> OTHER INFORMATION: Xaa = Any Amino Acid

<400> SEQUENCE: 4

Met Xaa Glu Thr Tyr Glu Leu Ile Ile His Pro Phe Asn Tyr Tyr Ala
1               5                   10                  15

<210> SEQ ID NO 5
<211> LENGTH: 16
<212> TYPE: PRT
<213> ORGANISM: M. sexta
<220> FEATURE:
<221> NAME/KEY: VARIANT
<222> LOCATION: (1)...(16)
<223> OTHER INFORMATION: Xaa = Any Amino Acid

<400> SEQUENCE: 5

Met Xaa Xaa Xaa His Gln Leu Pro Leu Ala Gln Asp Ile Lys Asn His
1               5                   10                  15
```

```
<210> SEQ ID NO 6
<211> LENGTH: 8
<212> TYPE: PRT
<213> ORGANISM: M. sexta
<220> FEATURE:
<221> NAME/KEY: VARIANT
<222> LOCATION: (1)...(8)
<223> OTHER INFORMATION: Xaa = Any Amino Acid

<400> SEQUENCE: 6

Met Xaa Xaa Val Xaa Val Asp Xaa
 1               5

<210> SEQ ID NO 7
<211> LENGTH: 9
<212> TYPE: PRT
<213> ORGANISM: M. sexta
<220> FEATURE:
<221> NAME/KEY: VARIANT
<222> LOCATION: (1)...(9)
<223> OTHER INFORMATION: Xaa = Any Amino Acid

<400> SEQUENCE: 7

Met Asn Phe Xaa Ser Val Asn Xaa Glu
 1               5

<210> SEQ ID NO 8
<211> LENGTH: 109
<212> TYPE: PRT
<213> ORGANISM: M. sexta

<400> SEQUENCE: 8

Glu Trp Val Met Pro Ile Phe Val Pro Glu Asn Gly Lys Gly Pro
 1               5                  10                  15

Phe Pro Gln Arg Leu Asn Gln Leu Lys Ser Asn Lys Asp Arg Gly Thr
                20                  25                  30

Lys Ile Phe Tyr Tyr Ser Ile Thr Gly Pro Gly Ala Asp Ser Pro Pro
                35                  40                  45

Glu Gly Val Phe Thr Ile Glu Lys Glu Ser Gly Trp Leu Leu Leu His
                50                  55                  60

Met Pro Leu Asp Arg Glu Lys Ile Val Lys Tyr Glu Leu Tyr Gly His
65                  70                  75                  80

Ala Val Ser Glu Asn Gly Ala Ser Val Glu Glu Pro Met Asn Ile Ser
                85                  90                  95

Ile Ile Val Thr Asp Gln Asn Asp Asn Lys Pro Lys Phe
                100                 105

<210> SEQ ID NO 9
<211> LENGTH: 105
<212> TYPE: PRT
<213> ORGANISM: M. sexta

<400> SEQUENCE: 9

Glu Asp Thr Val Tyr Ser Phe Asp Ile Asp Glu Asn Ala Gln Arg Gly
 1               5                  10                  15

Tyr Gln Val Gly Gln Ile Val Ala Arg Asp Ala Asp Leu Gly Gln Asn
                20                  25                  30

Ala Gln Leu Ser Tyr Gly Val Val Ser Asp Trp Ala Asn Asp Val Phe
                35                  40                  45

Ser Leu Asn Pro Gln Thr Gly Met Leu Thr Leu Thr Ala Arg Leu Asp
                50                  55                  60
```

-continued

```
Tyr Glu Glu Val Gln His Tyr Ile Leu Ile Val Gln Ala Gln Asp Asn
 65              70                  75                  80

Gly Gln Pro Ser Leu Ser Thr Thr Ile Thr Val Tyr Cys Asn Val Leu
             85                  90                  95

Asp Leu Asn Asp Asn Ala Pro Ile Phe
            100             105
```

<210> SEQ ID NO 10
<211> LENGTH: 92
<212> TYPE: PRT
<213> ORGANISM: M. sexta

<400> SEQUENCE: 10

```
Ala Ser Pro Val Ile Thr Leu Ala Ile Pro Glu Asn Thr Asn Gly Ser
 1               5                  10                  15

Leu Phe Pro Ile Pro Leu Ala Ser Asp Arg Asp Ala Asn Glu Leu Gln
             20                  25                  30

Val Ala Glu Asp Gln Glu Glu Lys Gln Pro Gln Leu Ile Val Met Gly
             35                  40                  45

Asn Leu Asp Arg Glu Arg Trp Asp Ser Tyr Asp Leu Thr Ile Lys Val
     50                  55                  60

Gln Asp Gly Gly Ser Pro Pro Arg Ala Thr Ser Ala Leu Leu Arg Val
 65              70                  75                  80

Thr Val Leu Asp Thr Asn Asp Asn Ala Pro Lys Phe
             85                  90
```

<210> SEQ ID NO 11
<211> LENGTH: 106
<212> TYPE: PRT
<213> ORGANISM: M. sexta

<400> SEQUENCE: 11

```
Ile Val Thr Glu Asn Ile Trp Lys Ala Pro Lys Pro Val Glu Met Val
 1               5                  10                  15

Glu Asn Ser Thr Pro His Pro Ile Lys Ile Thr Gln Val Arg Trp Asn
             20                  25                  30

Asp Pro Gly Ala Gln Tyr Ser Leu Val Asp Lys Glu Lys Leu Pro Arg
             35                  40                  45

Phe Pro Phe Ser Ile Asp Gln Glu Gly Asp Ile Tyr Val Thr Gln Pro
     50                  55                  60

Ile Asp Arg Glu Leu Lys Asp Ala Tyr Val Phe Tyr Ala Val Ala Lys
 65              70                  75                  80

Asp Glu Tyr Gly Lys Pro Leu Ser Tyr Pro Leu Glu Ile His Val Lys
             85                  90                  95

Val Lys Asp Asn Asp Asn Pro Pro Thr Cys
            100             105
```